US012629203B2

(12) United States Patent
Okarski et al.

(10) Patent No.: US 12,629,203 B2
(45) Date of Patent: May 19, 2026

(54) ELONGATED TRAPEZOIDAL ELECTRODES OF A BASKET CATHETER AND METHODS OF MAKING THE SAME

(71) Applicant: Biosense Webster (Israel) Ltd., Yokneam (IL)

(72) Inventors: Kevin Mark Okarski, Monrovia, CA (US); Keshava Datta, Chino Hills, CA (US); Abubakarr Bah, Irvine, CA (US); Thanh Nguyen, El Monte, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 428 days.

(21) Appl. No.: 18/169,822

(22) Filed: Feb. 15, 2023

(65) Prior Publication Data

US 2023/0301712 A1     Sep. 28, 2023

Related U.S. Application Data

(60) Provisional application No. 63/323,807, filed on Mar. 25, 2022.

(51) Int. Cl.
| | |
|---|---|
| *A61B 18/14* | (2006.01) |
| *A61B 17/00* | (2006.01) |
| *A61B 18/00* | (2006.01) |

(52) U.S. Cl.
CPC ..................... *A61B 18/1492* (2013.01); *A61B 2017/00185* (2013.01); *A61B 2017/00526* (2013.01);

(Continued)

(58) Field of Classification Search
CPC ...... A61B 18/1492; A61B 2017/00185; A61B 2017/00526; A61B 2018/0016;

(Continued)

(56) References Cited

U.S. PATENT DOCUMENTS

| | | |
|---|---|---|
| 4,699,147 A | 10/1987 | Chilson et al. |
| 4,940,064 A | 7/1990 | Desai |

(Continued)

FOREIGN PATENT DOCUMENTS

| | | |
|---|---|---|
| CN | 111248993 A | 6/2020 |
| CN | 111248996 A | 6/2020 |

(Continued)

OTHER PUBLICATIONS

Partial European Search Report dated Aug. 4, 2023, from corresponding European Application No. 23163970.9.

(Continued)

*Primary Examiner* — Beverly M Flanagan

(57) ABSTRACT

The disclosed technology includes a medical probe comprising a tubular shaft extending along a longitudinal axis of the medical probe. The medical probe further comprises an expandable basket assembly coupled to the distal end of the tubular shaft. The basket assembly comprises a plurality of spines and a plurality of electrodes. The electrode comprises an electrode body that defines a lumen therethrough such that the respective spine extends through the lumen. The respective electrode body comprises two sections that define a lengthwise direction of the electrode body section that are inclined inward with respect to a central axis of the respective electrode.

16 Claims, 19 Drawing Sheets

(52) U.S. Cl.
CPC ................. *A61B 2018/0016* (2013.01); *A61B 2018/00267* (2013.01); *A61B 2018/00351* (2013.01); *A61B 2018/00577* (2013.01); *A61B 2018/00613* (2013.01); *A61B 2018/00767* (2013.01); *A61B 2018/1405* (2013.01)

(58) Field of Classification Search
CPC ........... A61B 2018/00267; A61B 2018/00351; A61B 2018/00577; A61B 2018/00613; A61B 2018/00767; A61B 2018/1405; A61B 2018/1467
USPC ........................................................ 606/41
See application file for complete search history.

(56) References Cited

U.S. PATENT DOCUMENTS

| | | | |
|---|---|---|---|
| 5,215,103 A | 6/1993 | Desai | |
| 5,255,679 A | 10/1993 | Imran | |
| 5,293,869 A | 3/1994 | Edwards et al. | |
| 5,309,910 A | 5/1994 | Edwards et al. | |
| 5,313,943 A | 5/1994 | Houser et al. | |
| 5,324,284 A | 6/1994 | Imran | |
| 5,345,936 A | 9/1994 | Pomeranz et al. | |
| 5,365,926 A | 11/1994 | Desai | |
| 5,396,887 A | 3/1995 | Imran | |
| 5,400,783 A | 3/1995 | Pomeranz et al. | |
| 5,411,025 A | 5/1995 | Webster, Jr. | |
| 5,415,166 A | 5/1995 | Imran | |
| 5,456,254 A | 10/1995 | Pietroski et al. | |
| 5,465,717 A | 11/1995 | Imran et al. | |
| 5,476,495 A | 12/1995 | Kordis et al. | |
| 5,499,981 A | 3/1996 | Kordis | |
| 5,526,810 A | 6/1996 | Wang | |
| 5,546,940 A | 8/1996 | Panescu et al. | |
| 5,549,108 A | 8/1996 | Edwards et al. | |
| 5,558,073 A | 9/1996 | Pomeranz et al. | |
| 5,577,509 A | 11/1996 | Panescu et al. | |
| 5,595,183 A | 1/1997 | Swanson et al. | |
| 5,598,848 A | 2/1997 | Swanson et al. | |
| 5,609,157 A | 3/1997 | Panescu et al. | |
| 5,628,313 A | 5/1997 | Webster, Jr. | |
| 5,681,280 A | 10/1997 | Rusk et al. | |
| 5,722,401 A | 3/1998 | Pietroski et al. | |
| 5,722,403 A | 3/1998 | McGee et al. | |
| 5,725,525 A | 3/1998 | Kordis | |
| 5,730,128 A | 3/1998 | Pomeranz et al. | |
| 5,772,590 A | 6/1998 | Webster, Jr. | |
| 5,782,899 A | 7/1998 | Imran | |
| 5,823,189 A | 10/1998 | Kordis | |
| 5,881,727 A | 3/1999 | Edwards | |
| 5,893,847 A | 4/1999 | Kordis | |
| 5,904,680 A | 5/1999 | Kordis et al. | |
| 5,911,739 A | 6/1999 | Kordis et al. | |
| 5,928,228 A | 7/1999 | Kordis et al. | |
| 5,968,040 A | 10/1999 | Swanson et al. | |
| 6,014,579 A | 1/2000 | Pomeranz et al. | |
| 6,014,590 A | 1/2000 | Whayne et al. | |
| 6,119,030 A | 9/2000 | Morency | |
| 6,142,993 A | 11/2000 | Whayne et al. | |
| 6,216,043 B1 | 4/2001 | Swanson et al. | |
| 6,216,044 B1 | 4/2001 | Kordis | |
| 6,428,537 B1 | 8/2002 | Swanson et al. | |
| 6,456,864 B1 | 9/2002 | Swanson et al. | |
| 6,574,492 B1 | 6/2003 | Ben-Haim et al. | |
| 6,584,345 B2 | 6/2003 | Govari | |
| 6,600,948 B2 | 7/2003 | Ben-Haim et al. | |
| 6,738,655 B1 | 5/2004 | Sen et al. | |
| 6,741,878 B2 | 5/2004 | Fuimaono et al. | |
| 6,748,255 B2 | 6/2004 | Fuimaono et al. | |
| 6,780,183 B2 | 8/2004 | Jimenez, Jr. et al. | |
| 6,837,886 B2 | 1/2005 | Collins et al. | |
| 6,866,662 B2 | 3/2005 | Fuimaono et al. | |
| 6,892,091 B1 | 5/2005 | Ben-Haim et al. | |
| 6,970,730 B2 | 11/2005 | Fuimaono et al. | |
| 6,973,340 B2 | 12/2005 | Fuimaono et al. | |
| 6,980,858 B2 | 12/2005 | Fuimaono et al. | |
| 7,048,734 B1 | 5/2006 | Fleischman et al. | |
| 7,149,563 B2 | 12/2006 | Fuimaono et al. | |
| 7,255,695 B2 | 8/2007 | Falwell et al. | |
| 7,257,434 B2 | 8/2007 | Fuimaono et al. | |
| 7,399,299 B2 | 7/2008 | Daniel et al. | |
| 7,410,486 B2 | 8/2008 | Fuimaono et al. | |
| 7,522,950 B2 | 4/2009 | Fuimaono et al. | |
| RE41,334 E | 5/2010 | Beatty et al. | |
| 7,846,157 B2 | 12/2010 | Kozel | |
| 7,930,018 B2 | 4/2011 | Harlev et al. | |
| 8,007,495 B2 | 8/2011 | McDaniel et al. | |
| 8,048,063 B2 | 11/2011 | Aeby et al. | |
| 8,103,327 B2 | 1/2012 | Harlev et al. | |
| 8,167,845 B2 | 5/2012 | Wang et al. | |
| 8,224,416 B2 | 7/2012 | De La Rama et al. | |
| 8,235,988 B2 | 8/2012 | Davis et al. | |
| 8,346,339 B2 | 1/2013 | Kordis et al. | |
| 8,435,232 B2 | 5/2013 | Aeby et al. | |
| 8,447,377 B2 | 5/2013 | Harlev et al. | |
| 8,498,686 B2 | 7/2013 | Grunewald | |
| 8,517,999 B2 | 8/2013 | Pappone et al. | |
| 8,545,490 B2 | 10/2013 | Mihajlovic et al. | |
| 8,560,086 B2 | 10/2013 | Just et al. | |
| 8,567,265 B2 | 10/2013 | Aeby et al. | |
| 8,712,550 B2 | 4/2014 | Grunewald | |
| 8,755,861 B2 | 6/2014 | Harlev et al. | |
| 8,825,130 B2 | 9/2014 | Just et al. | |
| 8,906,011 B2 | 12/2014 | Gelbart et al. | |
| 8,945,120 B2 | 2/2015 | McDaniel et al. | |
| 8,979,839 B2 | 3/2015 | De La Rama et al. | |
| 9,037,264 B2 | 5/2015 | Just et al. | |
| 9,131,980 B2 | 9/2015 | Bloom | |
| 9,204,929 B2 | 12/2015 | Solis | |
| 9,277,960 B2 | 3/2016 | Weinkam et al. | |
| 9,314,208 B1 | 4/2016 | Altmann et al. | |
| 9,339,331 B2 | 5/2016 | Tegg et al. | |
| 9,486,282 B2 | 11/2016 | Solis | |
| 9,554,718 B2 | 1/2017 | Bar-Tal et al. | |
| D782,686 S | 3/2017 | Werneth et al. | |
| 9,585,588 B2 | 3/2017 | Marecki et al. | |
| 9,597,036 B2 | 3/2017 | Aeby et al. | |
| 9,687,297 B2 | 6/2017 | Just et al. | |
| 9,693,733 B2 | 7/2017 | Altmann et al. | |
| 9,782,099 B2 | 10/2017 | Williams et al. | |
| 9,788,895 B2 | 10/2017 | Solis | |
| 9,801,681 B2 | 10/2017 | Laske et al. | |
| 9,814,618 B2 | 11/2017 | Nguyen et al. | |
| 9,833,161 B2 | 12/2017 | Govari | |
| 9,894,756 B2 | 2/2018 | Weinkam et al. | |
| 9,895,073 B2 | 2/2018 | Solis | |
| 9,907,609 B2 | 3/2018 | Cao et al. | |
| 9,974,460 B2 | 5/2018 | Wu et al. | |
| 9,986,949 B2 | 6/2018 | Govari et al. | |
| 9,993,160 B2 | 6/2018 | Salvestro et al. | |
| 10,014,607 B1 | 7/2018 | Govari et al. | |
| 10,028,376 B2 | 7/2018 | Weinkam et al. | |
| 10,034,637 B2 | 7/2018 | Harlev et al. | |
| 10,039,494 B2 | 8/2018 | Altmann et al. | |
| 10,045,707 B2 | 8/2018 | Govari | |
| 10,078,713 B2 | 9/2018 | Auerbach et al. | |
| 10,111,623 B2 | 10/2018 | Jung et al. | |
| 10,130,420 B2 | 11/2018 | Basu et al. | |
| 10,136,828 B2 | 11/2018 | Houben et al. | |
| 10,143,394 B2 | 12/2018 | Solis | |
| 10,172,536 B2 | 1/2019 | Maskara et al. | |
| 10,182,762 B2 | 1/2019 | Just et al. | |
| 10,194,818 B2 | 2/2019 | Williams et al. | |
| 10,201,311 B2 | 2/2019 | Chou et al. | |
| 10,219,860 B2 | 3/2019 | Harlev et al. | |
| 10,219,861 B2 | 3/2019 | Just et al. | |
| 10,231,328 B2 | 3/2019 | Weinkam et al. | |
| 10,238,309 B2 | 3/2019 | Bar-Tal et al. | |
| 10,278,590 B2 | 5/2019 | Salvestro et al. | |
| D851,774 S | 6/2019 | Werneth et al. | |
| 10,314,505 B2 | 6/2019 | Williams et al. | |
| 10,314,507 B2 | 6/2019 | Govari et al. | |
| 10,314,648 B2 | 6/2019 | Ge et al. | |

(56)                    References Cited

U.S. PATENT DOCUMENTS

| | | |
|---|---|---|
| 10,314,649 B2 | 6/2019 | Bakos et al. |
| 10,349,855 B2 | 7/2019 | Zeidan et al. |
| 10,350,003 B2 | 7/2019 | Weinkam et al. |
| 10,362,991 B2 | 7/2019 | Tran et al. |
| 10,375,827 B2 | 8/2019 | Weinkam et al. |
| 10,376,170 B2 | 8/2019 | Quinn et al. |
| 10,376,221 B2 | 8/2019 | Iyun et al. |
| 10,398,348 B2 | 9/2019 | Osadchy et al. |
| 10,403,053 B2 | 9/2019 | Katz et al. |
| 10,441,188 B2 | 10/2019 | Katz et al. |
| 10,470,682 B2 | 11/2019 | Deno et al. |
| 10,470,714 B2 | 11/2019 | Altmann et al. |
| 10,482,198 B2 | 11/2019 | Auerbach et al. |
| 10,492,857 B2 | 12/2019 | Guggenberger et al. |
| 10,542,620 B2 | 1/2020 | Weinkam et al. |
| 10,575,743 B2 | 3/2020 | Basu et al. |
| 10,575,745 B2 | 3/2020 | Solis |
| 10,582,871 B2 | 3/2020 | Williams et al. |
| 10,582,894 B2 | 3/2020 | Ben Zrihem et al. |
| 10,596,346 B2 | 3/2020 | Aeby et al. |
| 10,602,947 B2 | 3/2020 | Govari et al. |
| 10,617,867 B2 | 4/2020 | Viswanathan et al. |
| 10,660,702 B2 | 5/2020 | Viswanathan et al. |
| 10,667,753 B2 | 6/2020 | Werneth et al. |
| 10,674,929 B2 | 6/2020 | Houben et al. |
| 10,681,805 B2 | 6/2020 | Weinkam et al. |
| 10,682,181 B2 | 6/2020 | Cohen et al. |
| 10,687,892 B2 | 6/2020 | Long et al. |
| 10,702,178 B2 | 7/2020 | Dahlen et al. |
| 10,716,477 B2 | 7/2020 | Salvestro et al. |
| 10,758,304 B2 | 9/2020 | Aujla |
| 10,765,371 B2 | 9/2020 | Hayam et al. |
| 10,772,566 B2 | 9/2020 | Aujila |
| 10,799,281 B2 | 10/2020 | Goertzen et al. |
| 10,842,558 B2 | 11/2020 | Harlev et al. |
| 10,842,561 B2 | 11/2020 | Viswanathan et al. |
| 10,863,914 B2 | 12/2020 | Govari et al. |
| 10,881,376 B2 | 1/2021 | Shemesh et al. |
| 10,898,139 B2 | 1/2021 | Guta et al. |
| 10,905,329 B2 | 2/2021 | Bar-Tal et al. |
| 10,912,484 B2 | 2/2021 | Ziv-Ari et al. |
| 10,918,306 B2 | 2/2021 | Govari et al. |
| 10,939,871 B2 | 3/2021 | Altmann et al. |
| 10,952,795 B2 | 3/2021 | Cohen et al. |
| 10,973,426 B2 | 4/2021 | Williams et al. |
| 10,973,461 B2 | 4/2021 | Baram et al. |
| 10,987,045 B2 | 4/2021 | Basu et al. |
| 11,006,902 B1 | 5/2021 | Bonyak et al. |
| 11,040,208 B1 | 6/2021 | Govari et al. |
| 11,045,628 B2 | 6/2021 | Beeckler et al. |
| 11,051,877 B2 | 7/2021 | Sliwa et al. |
| 11,109,788 B2 | 9/2021 | Rottmann et al. |
| 11,116,435 B2 | 9/2021 | Urman et al. |
| 11,129,574 B2 | 9/2021 | Cohen et al. |
| 11,160,482 B2 | 11/2021 | Solis |
| 11,164,371 B2 | 11/2021 | Yellin et al. |
| 2002/0198522 A1 | 12/2002 | Kordis |
| 2004/0210121 A1 | 10/2004 | Fuimaono et al. |
| 2006/0009689 A1 | 1/2006 | Fuimaono et al. |
| 2006/0009690 A1 | 1/2006 | Fuimaono et al. |
| 2006/0100669 A1 | 5/2006 | Fuimaono et al. |
| 2007/0093806 A1 | 4/2007 | Desai et al. |
| 2007/0276212 A1 | 11/2007 | Fuimaono et al. |
| 2008/0234564 A1 | 9/2008 | Beatty et al. |
| 2011/0118726 A1 | 5/2011 | de la Rama et al. |
| 2011/0160574 A1 | 6/2011 | Harlev et al. |
| 2011/0190625 A1 | 8/2011 | Harlev et al. |
| 2011/0245756 A1 | 10/2011 | Arora et al. |
| 2011/0301597 A1 | 12/2011 | McDaniel et al. |
| 2013/0090651 A1 | 4/2013 | Smith |
| 2013/0172872 A1 | 7/2013 | Subramaniam et al. |
| 2013/0172883 A1 | 7/2013 | Lopes et al. |
| 2013/0178850 A1 | 7/2013 | Lopes et al. |
| 2013/0190587 A1 | 7/2013 | Lopes et al. |
| 2013/0296852 A1 | 11/2013 | Madjarov et al. |
| 2014/0025069 A1 | 1/2014 | Willard et al. |
| 2014/0052118 A1 | 2/2014 | Laske et al. |
| 2014/0180147 A1 | 6/2014 | Thakur et al. |
| 2014/0180151 A1 | 6/2014 | Maskara et al. |
| 2014/0180152 A1 | 6/2014 | Maskara et al. |
| 2014/0257069 A1 | 9/2014 | Eliason et al. |
| 2014/0276712 A1 | 9/2014 | Mallin et al. |
| 2014/0288552 A1 | 9/2014 | Kunis et al. |
| 2014/0309512 A1 | 10/2014 | Govari et al. |
| 2015/0011991 A1 | 1/2015 | Buysman et al. |
| 2015/0045863 A1 | 2/2015 | Litscher et al. |
| 2015/0080693 A1 | 3/2015 | Solis |
| 2015/0105770 A1 | 4/2015 | Amit |
| 2015/0119878 A1 | 4/2015 | Heisel et al. |
| 2015/0133919 A1 | 5/2015 | McDaniel et al. |
| 2015/0208942 A1 | 7/2015 | Bar-Tal et al. |
| 2015/0250424 A1 | 9/2015 | Govari et al. |
| 2015/0270634 A1 | 9/2015 | Buesseler et al. |
| 2015/0342532 A1 | 12/2015 | Basu et al. |
| 2016/0081746 A1 | 3/2016 | Solis |
| 2016/0113582 A1 | 4/2016 | Altmann et al. |
| 2016/0113709 A1 | 4/2016 | Maor |
| 2016/0183877 A1 | 6/2016 | Williams et al. |
| 2016/0228023 A1 | 8/2016 | Govari |
| 2016/0228062 A1 | 8/2016 | Altmann et al. |
| 2016/0278853 A1 | 9/2016 | Ogle et al. |
| 2016/0302858 A1 | 10/2016 | Bencini |
| 2016/0338770 A1 | 11/2016 | Bar-Tal et al. |
| 2017/0027638 A1 | 2/2017 | Solis |
| 2017/0065227 A1 | 3/2017 | Marrs et al. |
| 2017/0071543 A1 | 3/2017 | Basu et al. |
| 2017/0071544 A1 | 3/2017 | Basu et al. |
| 2017/0071665 A1 | 3/2017 | Solis |
| 2017/0095173 A1 | 4/2017 | Bar-Tal et al. |
| 2017/0100187 A1 | 4/2017 | Basu et al. |
| 2017/0143227 A1 | 5/2017 | Marecki et al. |
| 2017/0156790 A1 | 6/2017 | Aujla |
| 2017/0172442 A1 | 6/2017 | Govari |
| 2017/0185702 A1 | 6/2017 | Auerbach et al. |
| 2017/0202515 A1 | 7/2017 | Zrihem et al. |
| 2017/0221262 A1 | 8/2017 | Laughner et al. |
| 2017/0224958 A1 | 8/2017 | Cummings et al. |
| 2017/0265812 A1 | 9/2017 | Williams et al. |
| 2017/0281031 A1 | 10/2017 | Houben et al. |
| 2017/0281268 A1 | 10/2017 | Tran et al. |
| 2017/0296125 A1 | 10/2017 | Altmann et al. |
| 2017/0296251 A1 | 10/2017 | Wu et al. |
| 2017/0319140 A1 | 11/2017 | Wu et al. |
| 2017/0347959 A1 | 12/2017 | Guta et al. |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2018/0008203 A1 | 1/2018 | Iyun et al. |
| 2018/0028084 A1 | 2/2018 | Williams et al. |
| 2018/0049803 A1 | 2/2018 | Solis |
| 2018/0085064 A1 | 3/2018 | Auerbach et al. |
| 2018/0132749 A1 | 5/2018 | Govari et al. |
| 2018/0137687 A1 | 5/2018 | Katz et al. |
| 2018/0160936 A1 | 6/2018 | Govari et al. |
| 2018/0160978 A1 | 6/2018 | Cohen et al. |
| 2018/0168511 A1 | 6/2018 | Hall et al. |
| 2018/0184982 A1 | 7/2018 | Basu et al. |
| 2018/0192958 A1 | 7/2018 | Wu |
| 2018/0206792 A1 | 7/2018 | Auerbach et al. |
| 2018/0235692 A1 | 8/2018 | Efimov et al. |
| 2018/0249959 A1 | 9/2018 | Osypka |
| 2018/0256109 A1 | 9/2018 | Wu et al. |
| 2018/0279954 A1 | 10/2018 | Hayam et al. |
| 2018/0303414 A1 | 10/2018 | Toth et al. |
| 2018/0310987 A1 | 11/2018 | Altmann et al. |
| 2018/0311497 A1 | 11/2018 | Viswanathan et al. |
| 2018/0338722 A1 | 11/2018 | Altmann et al. |
| 2018/0344188 A1 | 12/2018 | Govari |
| 2018/0344202 A1 | 12/2018 | Bar-Tal et al. |
| 2018/0344251 A1 | 12/2018 | Harlev et al. |
| 2018/0344393 A1 | 12/2018 | Gruba et al. |
| 2018/0360534 A1 | 12/2018 | Teplitsky et al. |
| 2018/0365355 A1 | 12/2018 | Auerbach et al. |
| 2019/0000540 A1 | 1/2019 | Cohen et al. |

(56) References Cited

U.S. PATENT DOCUMENTS

| | | |
|---|---|---|
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Viswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0163707 A1 | 5/2020 | Sliwa et al. |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | DeSimone et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077180 A1 | 3/2021 | Govari et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0161592 A1 | 6/2021 | Altmann et al. |
| 2021/0162210 A1 | 6/2021 | Altmann et al. |
| 2021/0169421 A1 | 6/2021 | Govari |
| 2021/0169550 A1 | 6/2021 | Govari et al. |
| 2021/0169567 A1 | 6/2021 | Govari et al. |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0177503 A1 | 6/2021 | Altmann et al. |
| 2021/0178166 A1 | 6/2021 | Govari et al. |
| 2021/0186363 A1 | 6/2021 | Gliner et al. |
| 2021/0186604 A1 | 6/2021 | Altmann et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |
| 2022/0378498 A1 | 12/2022 | Zhang et al. |
| 2023/0190363 A1* | 6/2023 | Govari ............... A61B 18/1492 606/41 |

FOREIGN PATENT DOCUMENTS

| | | |
|---|---|---|
| CN | 113995501 A | 2/2022 |
| EP | 0668740 A1 | 8/1995 |
| EP | 0644738 B1 | 3/2000 |
| EP | 0727183 B1 | 11/2002 |
| EP | 0727184 B1 | 12/2002 |
| EP | 2783651 A1 | 10/2014 |
| EP | 2699151 B1 | 11/2015 |
| EP | 2699152 B1 | 11/2015 |
| EP | 2699153 B1 | 12/2015 |
| EP | 2498706 B1 | 4/2016 |
| EP | 2578173 B1 | 6/2017 |
| EP | 3238645 A1 | 11/2017 |
| EP | 2884931 B1 | 1/2018 |
| EP | 2349440 B1 | 8/2019 |
| EP | 3318211 B1 | 12/2019 |
| EP | 3581135 A1 | 12/2019 |
| EP | 2736434 B1 | 2/2020 |
| EP | 3451962 B1 | 3/2020 |
| EP | 3972510 A1 | 3/2022 |
| WO | 94/07412 A1 | 4/1994 |
| WO | 9421167 A1 | 9/1994 |
| WO | 9421169 A1 | 9/1994 |
| WO | 1994021167 A1 | 9/1994 |
| WO | 1994021169 A1 | 9/1994 |
| WO | 9625095 A1 | 8/1996 |
| WO | 1996025095 A1 | 8/1996 |
| WO | 9634560 A1 | 11/1996 |
| WO | 1996034560 A1 | 11/1996 |
| WO | 2001082814 A2 | 11/2001 |
| WO | 0182814 B1 | 5/2002 |
| WO | 2004087249 A2 | 10/2004 |
| WO | 2012100185 A2 | 7/2012 |
| WO | 2013052852 A1 | 4/2013 |
| WO | 2013162884 A1 | 10/2013 |
| WO | 2013173917 A1 | 11/2013 |
| WO | 2013176881 A1 | 11/2013 |
| WO | 2014176205 A1 | 10/2014 |
| WO | 2016019760 A1 | 2/2016 |
| WO | 2016044687 A1 | 3/2016 |
| WO | 2018111600 A1 | 6/2018 |

(56)     References Cited

FOREIGN PATENT DOCUMENTS

| WO | 2018191149 A1 | 10/2018 | |
|----|---------------|---------|---|
| WO | 2019084442 A1 | 5/2019 | |
| WO | 2019143960 A1 | 7/2019 | |
| WO | 2020026217 A1 | 2/2020 | |
| WO | 2020206328 A1 | 10/2020 | |
| WO | WO-2022231726 A1 * | 11/2022 | .............. A61B 1/05 |

OTHER PUBLICATIONS

Extended European Search Report dated Nov. 7, 2023, from corresponding European Application No. 23163970.9.

* cited by examiner

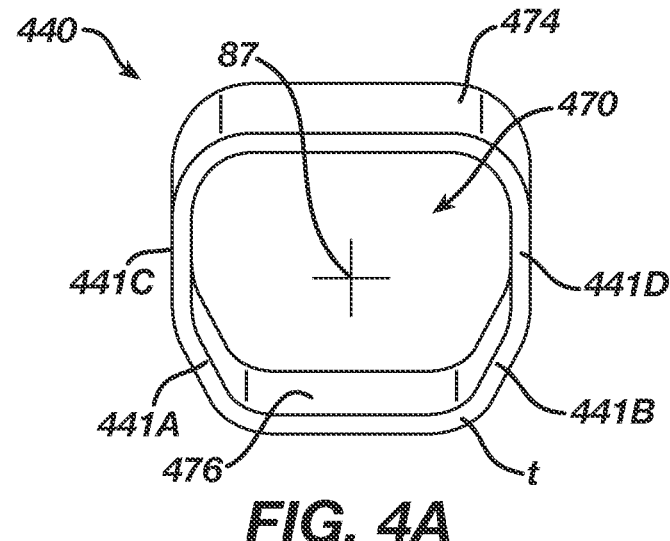
FIG. 4A
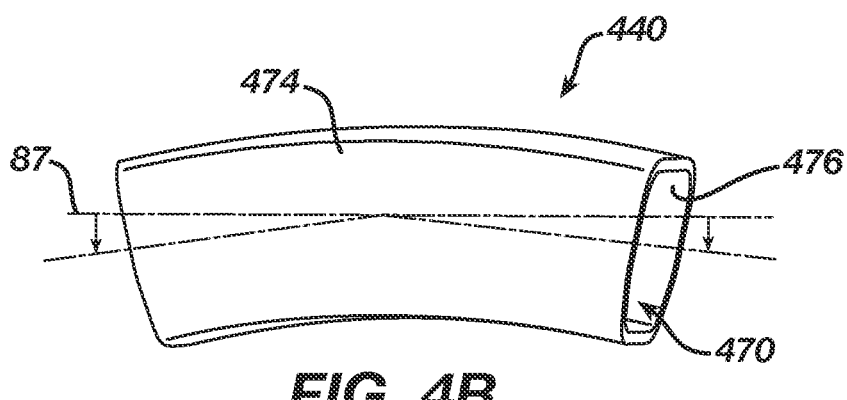
FIG. 4B
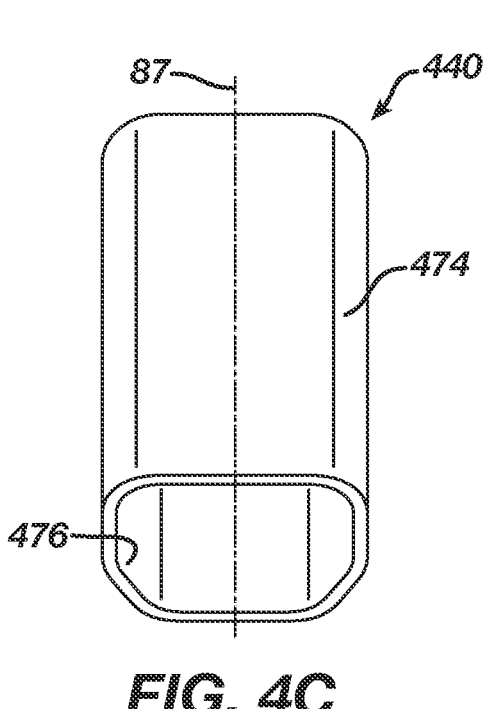
FIG. 4C
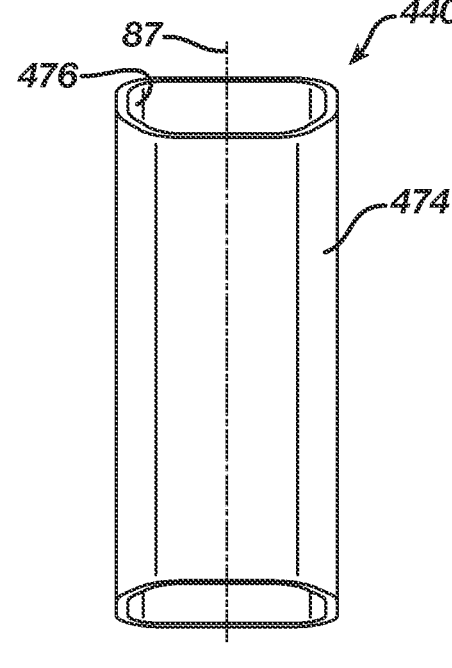
FIG. 4D

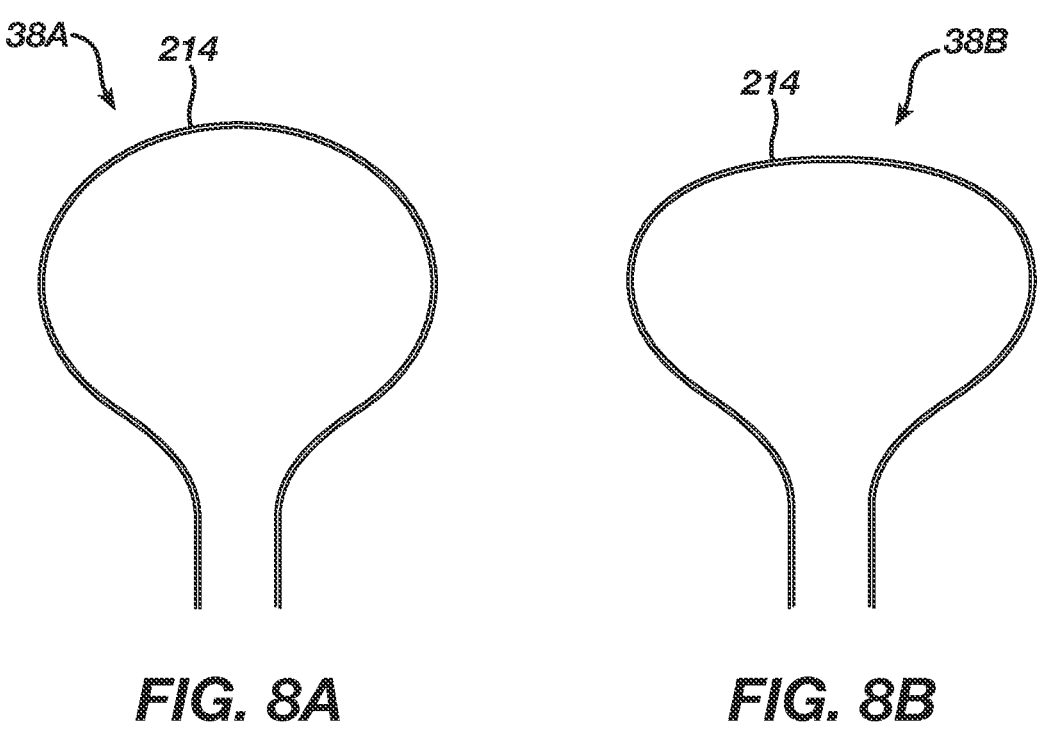
FIG. 8A          FIG. 8B
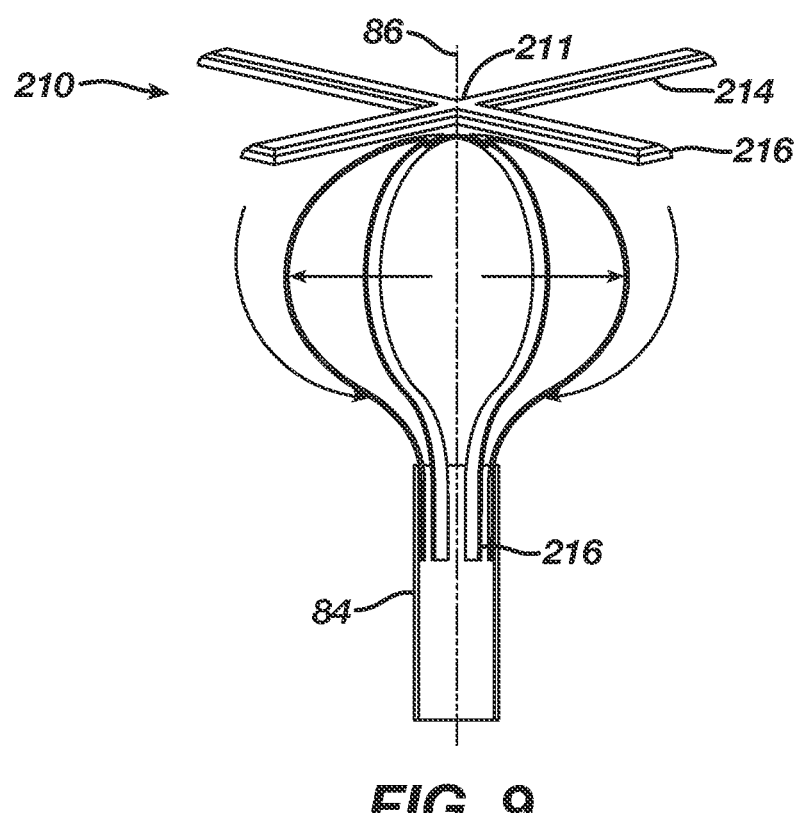
FIG. 9

210'

210'

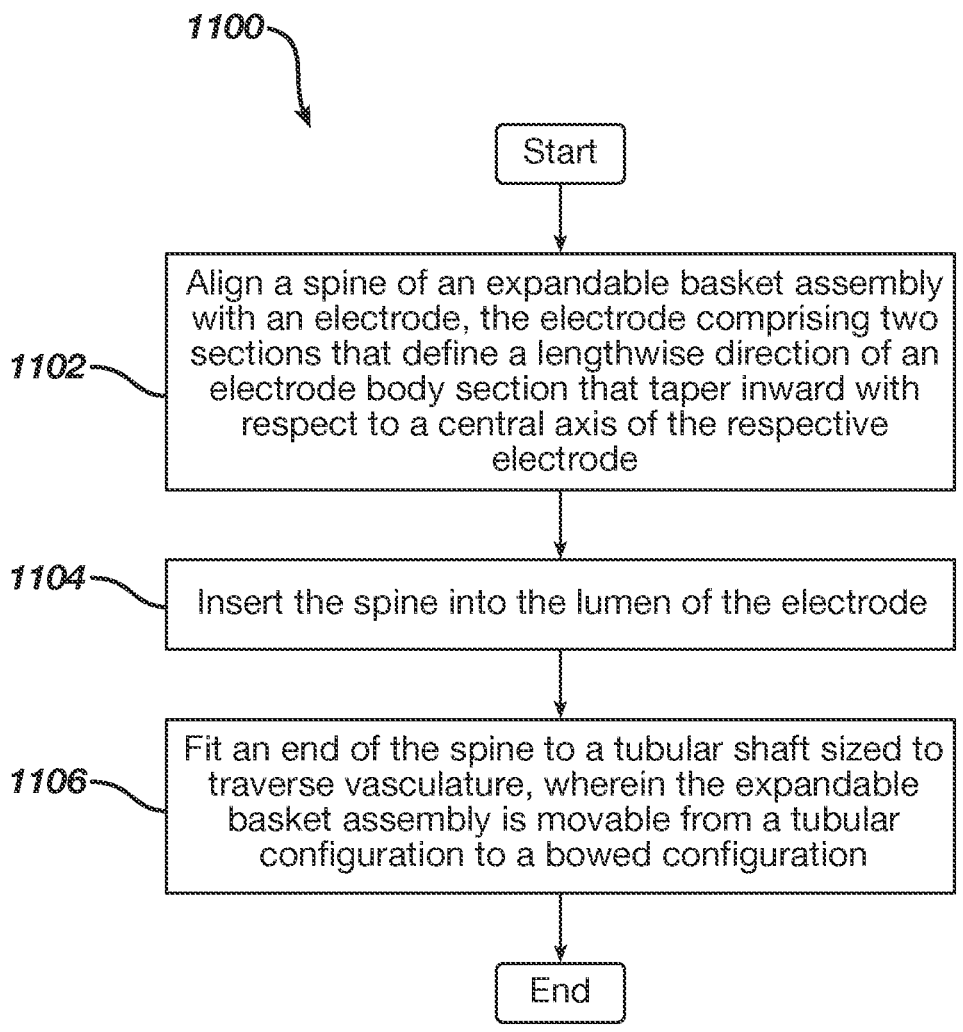

*1100*

Start

*1102*
Align a spine of an expandable basket assembly with an electrode, the electrode comprising two sections that define a lengthwise direction of an electrode body section that taper inward with respect to a central axis of the respective electrode

*1104*
Insert the spine into the lumen of the electrode

*1106*
Fit an end of the spine to a tubular shaft sized to traverse vasculature, wherein the expandable basket assembly is movable from a tubular configuration to a bowed configuration End

*FIG. 11*

ELONGATED TRAPEZOIDAL ELECTRODES OF A BASKET CATHETER AND METHODS OF MAKING THE SAME

CROSS REFERENCE TO RELATED APPLICATIONS

This application claims the benefit of priority under 35 U.S.C. § 119 to prior filed U.S. Provisional Application No. 63/323,807, filed on Mar. 25, 2022, the entire contents of which is incorporated herein by reference in its entirety as if fully set forth herein.

FIELD

The present invention relates generally to medical devices, and in particular catheters with trapezoidal electrodes, and further relates to, but not exclusively, catheters suitable for use to induce irreversible electroporation (IRE) of cardiac tissues.

BACKGROUND

Cardiac arrhythmias, such as atrial fibrillation (AF), occur when regions of cardiac tissue abnormally conduct electric signals to adjacent tissue. This disrupts the normal cardiac cycle and causes asynchronous rhythm. Certain procedures exist for treating arrhythmia, including surgically disrupting the origin of the signals causing the arrhythmia and disrupting the conducting pathway for such signals. By selectively ablating cardiac tissue by application of energy via a catheter, it is sometimes possible to cease or modify the propagation of unwanted electrical signals from one portion of the heart to another.

Many current ablation approaches in the art tend to utilize radiofrequency (RF) electrical energy to heat tissue. RF ablation can have certain rare drawbacks due to operator's skill, such as heightened risk of thermal cell injury which can lead to tissue charring, burning, steam pop, phrenic nerve palsy, pulmonary vein stenosis, and esophageal fistula. Cryoablation is an alternative approach to RF ablation that generally reduces thermal risks associated with RF ablation but may present tissue damage due to the very low temperature nature of such devices. Maneuvering cryoablation devices and selectively applying cryoablation, however, is generally more challenging compared to RF ablation; therefore cryoablation is not viable in certain anatomical geometries which may be reached by electrical ablation devices.

Some ablation approaches use irreversible electroporation (IRE) to ablate cardiac tissue using nonthermal ablation methods. IRE delivers short pulses of high voltage to tissues and generates an unrecoverable permeabilization of cell membranes. Delivery of IRE energy to tissues using multi-electrode catheters was previously proposed in the patent literature. Examples of systems and devices configured for IRE ablation are disclosed in U.S. Patent Pub. No. 2021/0169550A1, 2021/0169567A1, 2021/0169568A1, 2021/0161592A1, 2021/0196372A1, 2021/0177503A1, and 2021/0186604A1, each of which are incorporated herein by reference and attached in the appendix to priority application 63/323,807.

Regions of cardiac tissue can be mapped by a catheter to identify the abnormal electrical signals. The same or different catheter can be used to perform ablation. Some example catheters include a number of spines with electrodes positioned thereon. The electrodes are generally attached to the spines and secured in place by soldering, welding, or using an adhesive. Furthermore, multiple linear spines are generally assembled together by attaching both ends of the linear spines to a tubular shaft (e.g., a pusher tube) to form a spherical basket. Due to the small size of the spines and the electrodes, however, adhering the electrodes to the spines and then forming a spherical basket from the multiple linear spines can be a difficult task, increasing the manufacturing time and cost and the chances that the electrode fails due to an improper bond or misalignment. What is needed, therefore, are devices and methods of forming an improved basket assembly that can help to reduce the time required for manufacturing the basket assembly, alternative catheter geometries, and alternative electrode shapes and sizes in general.

SUMMARY

Various embodiments of a medical probe and related methods are described and illustrated. The medical probe may include a tubular shaft including a proximal end and a distal end. The tubular shaft can extend along a longitudinal axis of the medical probe. The medical probe can include an expandable basket assembly proximate the distal end of the tubular shaft. The basket assembly can include a plurality of spines extending along the longitudinal axis and converging at a central spine intersection. The central spine intersection can include one or more cutouts that allows for the spines to bow radially outward from the longitudinal axis when the expandable basket assembly is transitioned from a collapsed form to an expanded form. Each spine of the plurality of spines can include a plurality of electrodes. The respective electrode can include an electrode body that defines a lumen therethrough such that the respective spine can extend through the electrode body lumen. The respective electrode body can include two sections that define a lengthwise direction of the electrode body section that are inclined inward with respect to a central axis of the respective electrode.

BRIEF DESCRIPTION OF THE DRAWINGS

FIGS. 4A-4F are schematic pictorial illustrations showing a perspective view of various example electrodes, in accordance with embodiments of the present invention;

FIGS. 8A and 8B are schematic pictorial illustrations showing a profile outline of a basket assembly of a given medical device, in accordance with embodiments of the present invention;

FIG. 9 is a schematic pictorial illustration showing a side view of a plurality of spines forming a basket assembly, in accordance with an embodiment of the present invention;

FIG. 11 is a flowchart illustrating another method of assembling a basket assembly, in accordance with an embodiment of the present invention.

DETAILED DESCRIPTION

Figure 1:
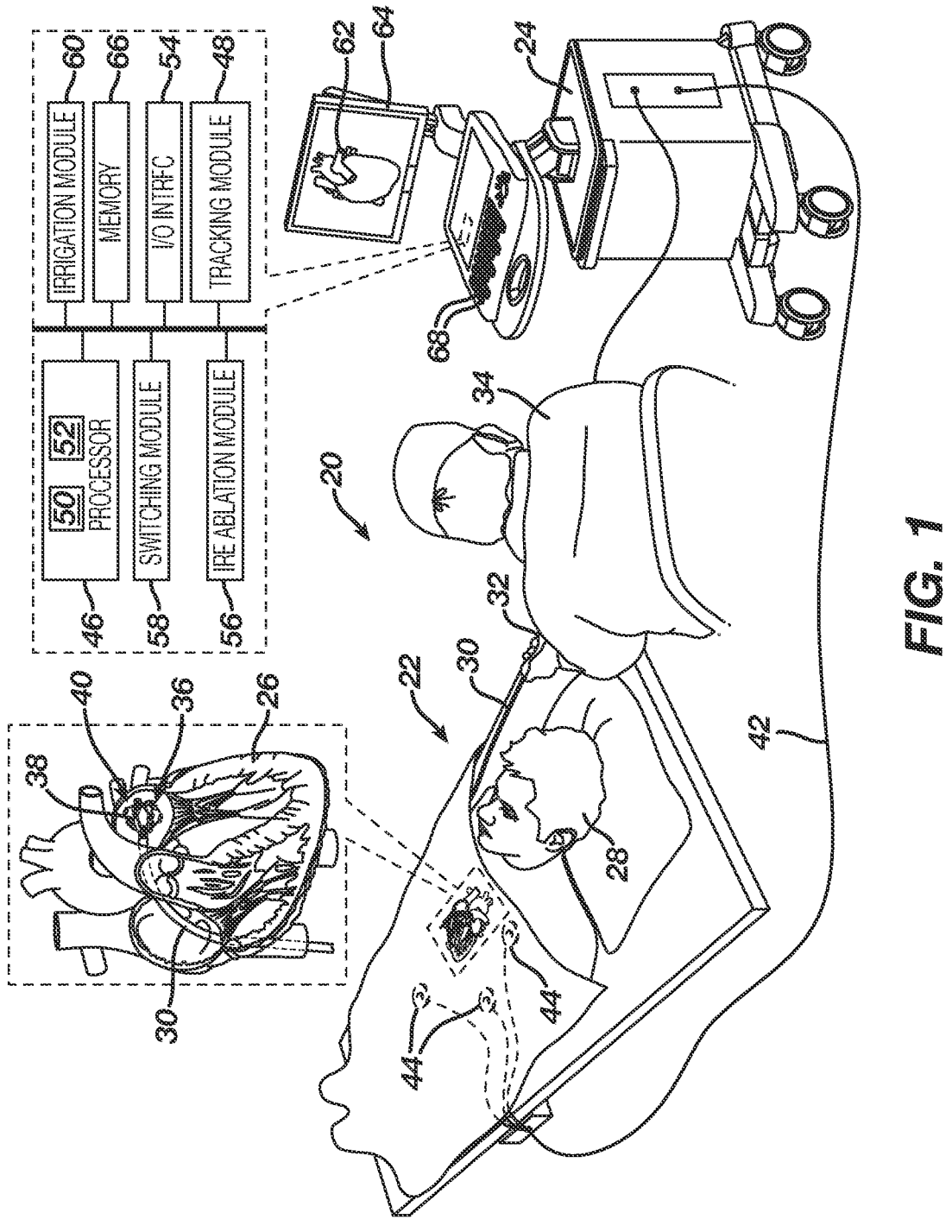
FIG. 1 is a schematic pictorial illustration of a medical system including a medical probe whose distal end includes a basket assembly with electrodes, in accordance with an embodiment of the present invention.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 110%.

As used herein, the terms "patient," "host," "user," and "subject" refer to any human or animal subject and are not intended to limit the systems or methods to human use, although use of the subject invention in a human patient represents a preferred embodiment. In addition, vasculature of a "patient," "host," "user," and "subject" can be vasculature of a human or any animal. It should be appreciated that an animal can be a variety of any applicable type, including, but not limited thereto, mammal, veterinarian animal, livestock animal or pet type animal, etc. As an example, the animal can be a laboratory animal specifically selected to have certain characteristics similar to a human (e.g., rat, dog, pig, monkey, or the like). It should be appreciated that the subject can be any applicable human patient, for example. As well, the term "proximal" indicates a location closer to the operator or physician whereas "distal" indicates a location further away to the operator or physician.

As discussed herein, "operator" can include a doctor, surgeon, technician, scientist, or any other individual or delivery instrumentation associated with delivery of a multi-electrode catheter for the treatment of drug refractory atrial fibrillation to a subject.

As discussed herein, the term "ablate" or "ablation", as it relates to the devices and corresponding systems of this disclosure, refers to components and structural features configured to reduce or prevent the generation of erratic cardiac signals in the cells by utilizing non-thermal energy, such as irreversible electroporation (IRE), referred throughout this disclosure interchangeably as pulsed electric field (PEF) and pulsed field ablation (PFA). Ablating or ablation as it relates to the devices and corresponding systems of this disclosure is used throughout this disclosure in reference to non-thermal ablation of cardiac tissue for certain conditions including, but not limited to, arrhythmias, atrial flutter ablation, pulmonary vein isolation, supraventricular tachycardia ablation, and ventricular tachycardia ablation. The term "ablate" or "ablation" also includes known methods, devices, and systems to achieve various forms of bodily tissue ablation as understood by a person skilled in the relevant art.

As discussed herein, the terms "bipolar" and "unipolar" when used to refer to ablation schemes describe ablation schemes which differ with respect to electrical current path and electric field distribution. "Bipolar" refers to ablation scheme utilizing a current path between two electrodes that are both positioned at a treatment site; current density and electric flux density is typically approximately equal at each of the two electrodes. "Unipolar" refers to ablation scheme utilizing a current path between two electrodes where one electrode including a high current density and high electric flux density is positioned at a treatment site, and a second electrode including comparatively lower current density and lower electric flux density is positioned remotely from the treatment site.

As discussed herein, the terms "biphasic pulse" and "monophasic pulse" refer to respective electrical signals. "Biphasic pulse" refers to an electrical signal including a positive-voltage phase pulse (referred to herein as "positive phase") and a negative-voltage phase pulse (referred to herein as "negative phase"). "Monophasic pulse" refers to an electrical signal including only a positive or only a negative phase. Preferably, a system providing the biphasic pulse is configured to prevent application of a direct current voltage (DC) to a patient. For instance, the average voltage of the biphasic pulse can be zero volts with respect to ground or other common reference voltage. Additionally, or alternatively, the system can include a capacitor or other protective component. Where voltage amplitude of the biphasic and/or monophasic pulse is described herein, it is understood that the expressed voltage amplitude is an absolute value of the approximate peak amplitude of each of the positive-voltage phase and/or the negative-voltage phase. Each phase of the biphasic and monophasic pulse preferably has a square shape including an essentially constant voltage amplitude during a majority of the phase duration. Phases of the biphasic pulse are separated in time by an interphase delay. The interphase delay duration is preferably less than or approximately equal to the duration of a phase of the biphasic pulse. The interphase delay duration is more preferably about 25% of the duration of the phase of the biphasic pulse.

As discussed herein, the terms "tubular" and "tube" are to be construed broadly and are not limited to a structure that is a right cylinder or strictly circumferential in cross-section or of a uniform cross-section throughout its length. For example, the tubular structures are generally illustrated as a substantially right cylindrical structure. However, the tubular structures may have a tapered or curved outer surface without departing from the scope of the present disclosure.

The term "temperature rating", as used herein, is defined as the maximum continuous temperature that a component can withstand during its lifetime without causing thermal damage, such as melting or thermal degradation (e.g., charring and crumbling) of the component.

The present disclosure is related to systems, methods or uses and devices which utilize end effectors including electrodes affixed to spines. Example systems, methods, and devices of the present disclosure may be particularly suited for IRE ablation of cardiac tissue to treat cardiac arrhythmias. Ablative energies are typically provided to cardiac tissue by a tip portion of a catheter which can deliver ablative energy alongside the tissue to be ablated. Some example catheters include three-dimensional structures at the tip portion and are configured to administer ablative energy from various electrodes positioned on the three-dimensional structures. Ablative procedures incorporating such example catheters can be visualized using fluoroscopy.

Ablation of cardiac tissue using application of a thermal technique, such as radio frequency (RF) energy and cryoablation, to correct a malfunctioning heart is a well-known procedure. Typically, to successfully ablate using a thermal technique, cardiac electropotentials need to be measured at various locations of the myocardium. In addition, temperature measurements during ablation provide data enabling the efficacy of the ablation. Typically, for an ablation procedure using a thermal technique, the electropotentials and the temperatures are measured before, during, and after the actual ablation.

RF approaches can have risks that can lead to tissue charring, burning, steam pop, phrenic nerve palsy, pulmonary vein stenosis, and esophageal fistula. Cryoablation is an alternative approach to RF ablation that can reduce some thermal risks associated with RF ablation. However maneuvering cryoablation devices and selectively applying cryoablation is generally more challenging compared to RF ablation; therefore, cryoablation is not viable in certain anatomical geometries which may be reached by electrical ablation devices.

IRE as discussed in this disclosure is a non-thermal cell death technology that can be used for ablation of atrial arrhythmias. To ablate using IRE/PEF, biphasic voltage pulses are applied to disrupt cellular structures of myocardium. The biphasic pulses are non-sinusoidal and can be tuned to target cells based on electrophysiology of the cells. In contrast, to ablate using RF, a sinusoidal voltage waveform is applied to produce heat at the treatment area, indiscriminately heating all cells in the treatment area. IRE therefore has the capability to spare adjacent heat sensitive structures or tissues which would be of benefit in the reduction of possible complications known with ablation or isolation modalities. Additionally, or alternatively, monophasic pulses can be utilized.

Electroporation can be induced by applying a pulsed electric field across biological cells to cause reversable (temporary) or irreversible (permanent) creation of pores in the cell membrane. The cells have a transmembrane electrostatic potential that is increased above a resting potential upon application of the pulsed electric field. While the transmembrane electrostatic potential remains below a threshold potential, the electroporation is reversable, meaning the pores can close when the applied pulse electric field is removed, and the cells can self-repair and survive. If the transmembrane electrostatic potential increases beyond the threshold potential, the electroporation is irreversible, and the cells become permanently permeable. As a result, the cells die due to a loss of homeostasis and typically die by programmed cell death or apoptosis, which is believed to leave less scar tissue as compared to other ablation modalities. Generally, cells of differing types have differing threshold potential. For instance, heart cells have a threshold potential of approximately 500 V/cm, whereas for bone it is 3000 V/cm. These differences in threshold potential allow IRE to selectively target tissue based on threshold potential.

The solution of this disclosure includes systems and methods for applying electrical signals from catheter electrodes positioned in the vicinity of myocardial tissue, preferably by applying a pulsed electric field effective to induce electroporation in the myocardial tissue. The systems and methods can be effective to ablate targeted tissue by inducing irreversible electroporation. In some examples, the systems and methods can be effective to induce reversible electroporation as part of a diagnostic procedure. Reversible electroporation occurs when the electricity applied with the electrodes is below the electric field threshold of the target tissue allowing cells to repair. Reversible electroporation does not kill the cells but allows a physician to see the effect of reversible electroporation on electrical activation signals in the vicinity of the target location. Example systems and methods for reversible electroporation is disclosed in U.S. Patent Publication 2021/0162210, the entirety of which are incorporated herein by reference and attached in the appendix to priority application 63/323,807.

The pulsed electric field, and its effectiveness to induce reversible and/or irreversible electroporation, can be affected by physical parameters of the system and biphasic pulse parameters of the electrical signal. Physical parameters can include electrode contact area, electrode spacing, electrode geometry, etc. examples presented herein generally include physical parameters adapted to effectively induce reversible and/or irreversible electroporation. Biphasic pulse parameters of the electrical signal can include voltage amplitude, pulse duration, pulse interphase delay, inter-pulse delay, total application time, delivered energy, etc. In some examples, parameters of the electrical signal can be adjusted to induce both reversible and irreversible electroporation given the same physical parameters. Examples of various systems and methods of ablation including IRE are presented in U.S. Patent Publications 2021/0169550A1, 2021/0169567A1, 2021/0169568A1, 2021/0161592A1, 2021/0196372A1, 2021/0177503A1, and 2021/0186604A1, the entirety of which are incorporated herein by reference and attached in the appendix to priority application 63/323,807.

To deliver pulsed field ablation (PFA) in an IRE (irreversible electroporation) procedure, electrodes should contact the tissue being ablated with a sufficiently large surface area. As described hereinbelow, the medical probe includes a tubular shaft including proximal and distal ends, and a basket assembly at the distal end of the tubular shaft. The basket assembly includes a single unitary structure. The unitary structure can include a plurality of linear spines formed from a planar sheet of material and one or more electrodes coupled to each of the spines. The plurality of linear spines can converge at a central spine intersection including one or more cutouts. The cutouts can allow for bending of each spine such that the spines form an approximately spherical or oblate-spheroid basket assembly. It is noted that the cutouts (in various configurations described and illustrated in the specification) allows the basket to be compressed into a much smaller form factor when undeployed (or undergoing a retraction into a delivery sheath) without buckling or plastic deformation.

FIG. 1 is a schematic, pictorial illustration of a medical system 20 including a medical probe 22 and a control console 24, in accordance with an embodiment of the present invention. Medical system 20 may be based, for example, on the CARTO® system, produced by Biosense Webster Inc. of 31 Technology Drive, Suite 200, Irvine, CA 92618 USA. In embodiments described hereinbelow, medical probe 22 can be used for diagnostic or therapeutic treatment, such as for performing ablation procedures in a heart 26 of a patient 28. Alternatively, medical probe 22 may be used, mutatis mutandis, for other therapeutic and/or diagnostic purposes in the heart or in other body organs.

Medical probe 22 includes a flexible insertion tube 30 and a handle 32 coupled to a proximal end of the tubular shaft. During a medical procedure, a medical professional 34 can insert probe 22 through the vascular system of patient 28 so that a distal end 36 of the medical probe enters a body cavity such as a chamber of heart 26. Upon distal end 36 entering the chamber of heart 26, medical professional 34 can deploy a basket assembly 38 approximate a distal end 36 of the medical probe 22. Basket assembly 38 can include a plurality of electrodes 40 affixed to a plurality of spines 214, as described in the description referencing FIGS. 2A and 2B hereinbelow. To start performing a medical procedure such as irreversible electroporation (IRE) ablation, medical professional 34 can manipulate handle 32 to position distal end 36 so that electrodes 40 engage cardiac tissue at a desired location or locations. Upon positioning the distal end 36 so that electrodes 40 engages cardiac tissue, the medical professional 34 can activate the medical probe 22 such that electrical pulses are delivered by the electrodes 40 to perform the IRE ablation.

The medical probe 22 can include a guide sheath and a therapeutic catheter, wherein the guide sheath includes the flexible insertion tube 30 and the handle 32 and the therapeutic catheter includes the basket assembly 38, electrodes 40, and a tubular shaft 84 (see FIGS. 2 through 4). The therapeutic catheter is translated through the guide sheath so that the basket assembly 38 is positioned in the heart 26. The distal end 36 of the medical probe 22 corresponds to a distal end of the guide sheath when the basket assembly 38 is contained within the flexible insertion tube 30, and the distal end 36 of the medical probe 22 corresponds to a distal end of the basket assembly 38 when the basket assembly 38 is extended from the distal end of the guide sheath. The medical probe 22 can be alternatively configured to include a second handle on the therapeutic catheter and other features as understood by a person skilled in the pertinent art.

In the configuration shown in FIG. 1, control console 24 is connected, by a cable 42, to body surface electrodes, which typically include adhesive skin patches 44 that are affixed to patient 28. Control console 24 includes a processor 46 that, in conjunction with a tracking module 48, determines location coordinates of distal end 36 inside heart 26. Location coordinates can be determined based on electromagnetic position sensor output signals provided from the distal portion of the catheter when in the presence of a generated magnetic field. Location coordinates can additionally, or alternatively be based on impedances and/or currents measured between adhesive skin patches 44 and electrodes 40 that are affixed to basket assembly 38. In addition to being used as location sensors during a medical procedure, electrodes 40 may perform other tasks such as ablating tissue in the heart.

As described hereinabove, in conjunction with tracking module 48, processor 46 may determine location coordinates of distal end 36 inside heart 26 based on impedances and/or currents measured between adhesive skin patches 44 and electrodes 40. Such a determination is typically after a calibration process relating the impedances or currents to known locations of the distal end has been performed. While embodiments presented herein describe electrodes 40 that are preferably configured to deliver IRE ablation energy to tissue in heart 26, configuring electrodes 40 to deliver any other type of ablation energy to tissue in any body cavity is considered to be within the spirit and scope of the present invention. Furthermore, although described in the context of being electrodes 40 that are configured to deliver IRE ablation energy to tissue in the heart 26, one skilled in the art will appreciate that the disclosed technology can be applicable to electrodes used for mapping and/or determining various characteristics of an organ or other part of the patient's 28 body.

Processor 46 may include real-time noise reduction circuitry 50 typically configured as a field programmable gate array (FPGA), followed by an analog-to-digital (A/D) signal conversion integrated circuit 52. The processor can be programmed to perform one or more algorithms and uses circuitry 50 and circuit 52 as well as features of modules to enable the medical professional 34 to perform the IRE ablation procedure.

Control console 24 also includes an input/output (I/O) communications interface 54 that enables control console 24 to transfer signals from, and/or transfer signals to electrodes 40 and adhesive skin patches 44. In the configuration shown in FIG. 1, control console 24 additionally includes an IRE ablation module 56 and a switching module 58.

IRE ablation module 56 is configured to generate IRE pulses including peak power in the range of tens of kilowatts. In some examples, the electrodes 40 are configured to deliver electrical pulses including a peak voltage of at least 900 volts (V). The medical system 20 performs IRE ablation by delivering IRE pulses to electrodes 40. Preferably, the medical system 20 delivers biphasic pulses between electrodes 40 on the spine. Additionally, or alternatively, the medical system 20 delivers monophasic pulses between at least one of the electrodes 40 and a skin patch.

Figure 2A:
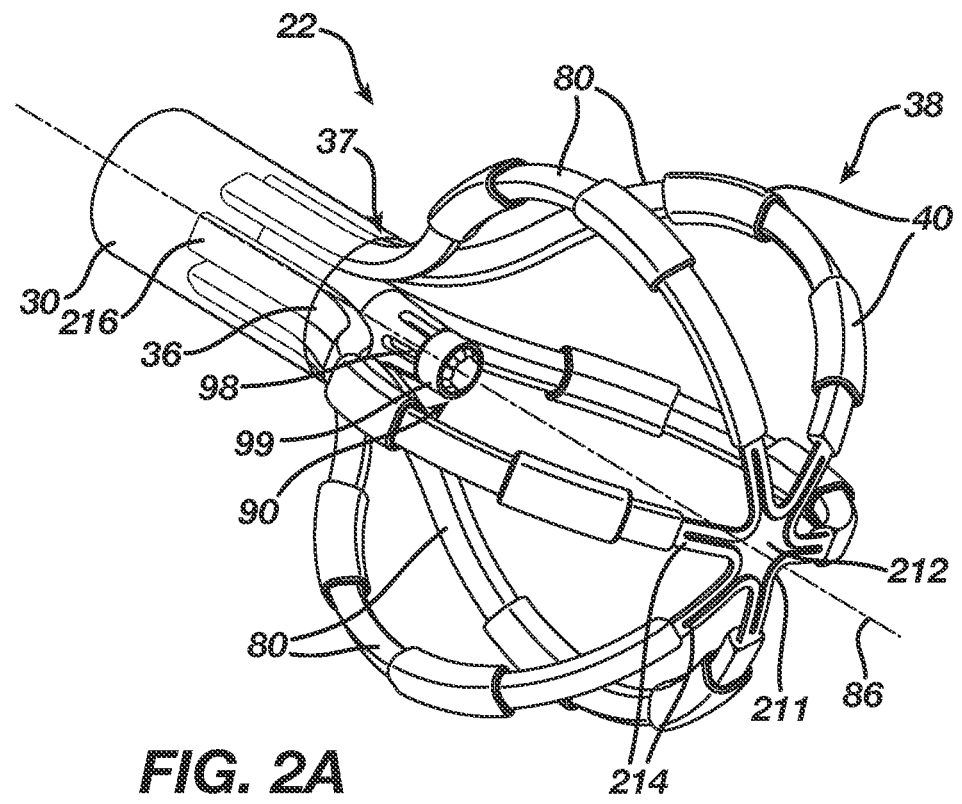
FIG. 2A is a schematic pictorial illustration showing a perspective view of a medical probe in an expanded form, in accordance with an embodiment of the present invention.
Figure 2B:
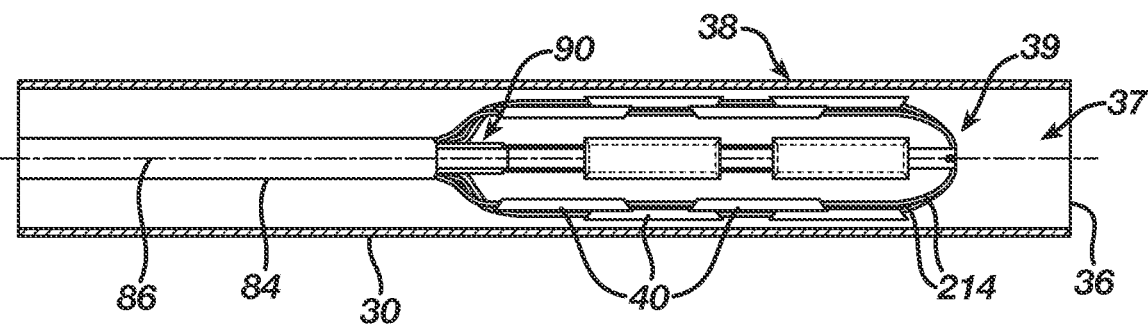
FIG. 2B is a schematic pictorial illustration showing a side view of a medical probe in a collapsed form, in accordance with embodiments of the present invention.
Figure 2C:
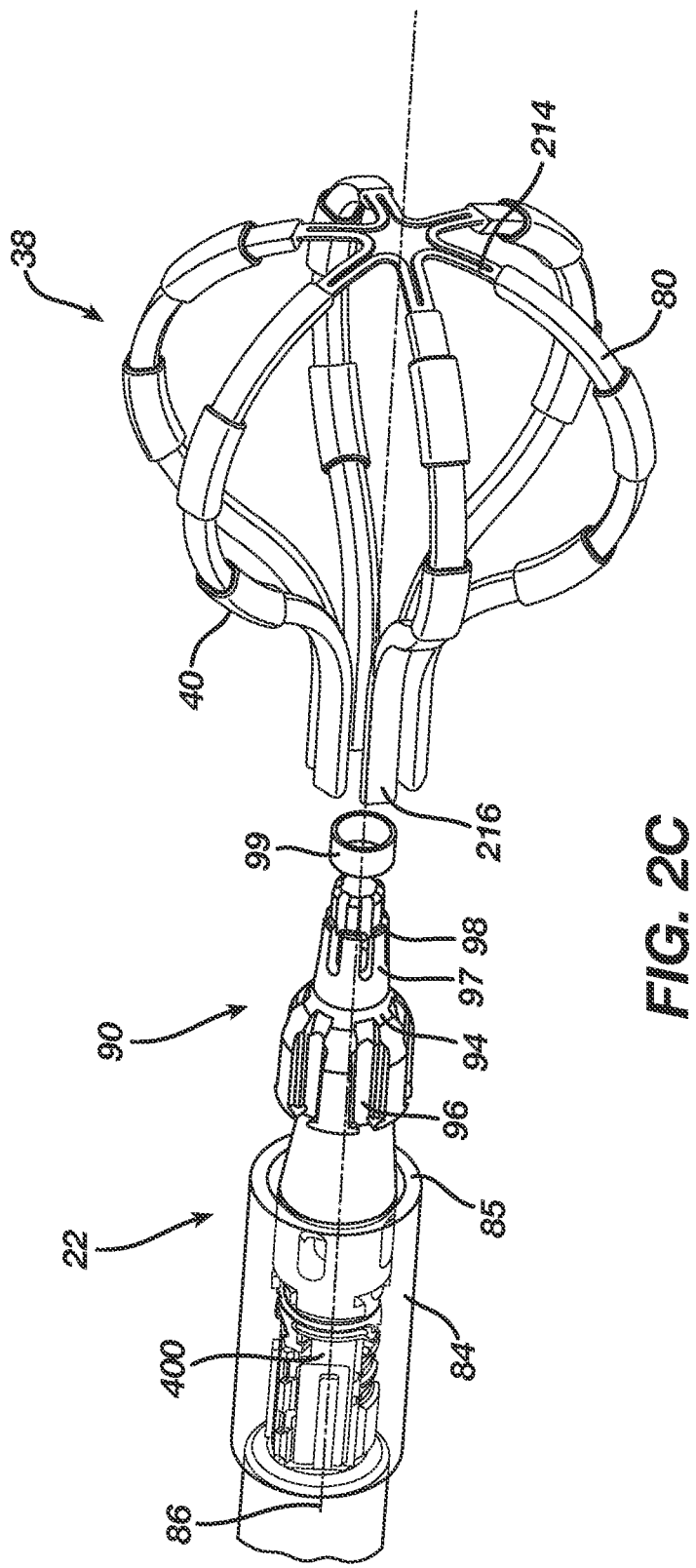
FIG. 2C is a schematic pictorial illustration showing an exploded side view of a medical probe, in accordance with an embodiment of the present invention.

In order to dissipate the heat and to improve the efficiency of the ablation process, system 20 supplies irrigation fluid (e.g., a saline solution) to distal end 36 and to the electrodes 40 via a channel (not shown) in tubular shaft 84 (see FIG. 2A through 2C). Additionally, or alternatively, irrigation fluid can be supplied through the flexible insertion tube 30. Control console 24 includes an irrigation module 60 to monitor and control irrigation parameters, such as the pressure and the temperature of the irrigation fluid. It is noted that while the preference for the exemplary embodiments of the medical probe is for IRE or PFA, it is within the scope of the present invention to also use the medical probe separately only for RF ablation (unipolar mode with an external grounding electrode or bipolar mode) or in combination with IRE and RF ablations sequentially (certain electrodes in IRE mode and other electrodes in RF mode) or simultaneously (groups of electrodes in IRE mode and other electrodes in RF mode).

Based on signals received from electrodes 40 and/or adhesive skin patches 44, processor 46 can generate an electroanatomical map 62 that shows the location of distal end 36 in the patient's body. During the procedure, processor 46 can present map 62 to medical professional 34 on a display 64, and store data representing the electroanatomical map in a memory 66. Memory 66 may include any suitable volatile and/or non-volatile memory, such as random-access memory or a hard disk drive.

In some embodiments, medical professional 34 can manipulate map 62 using one or more input devices 68. In alternative embodiments, display 64 may include a touchscreen that can be configured to accept inputs from medical professional 34, in addition to presenting map 62.

FIG. 2A is a schematic pictorial illustration showing a perspective view of a medical probe 22 including a basket assembly 38 in an expanded form when unconstrained, such as by being advanced out of an insertion tube lumen 80 at a distal end 36 of an insertion tube 30. The medical probe 22 illustrated in FIG. 2A lacks the guide sheath illustrated in FIG. 1. FIG. 2B shows the basket assembly in a collapsed form within insertion tube 30 of the guide sheath. In the expanded form (FIG. 2A), spines 214 bow radially outwardly and in the collapsed form (FIG. 2B) the spines are arranged generally along a longitudinal axis 86 of insertion tube 30.

As shown in FIG. 2A, basket assembly 38 includes a plurality of flexible spines 214 that are formed at the end of a tubular shaft 84 and are connected at both ends. During a medical procedure, medical professional 34 can deploy basket assembly 38 by extending tubular shaft 84 from insertion tube 30 causing basket assembly 38 to exit insertion tube 30 and transition to the expanded form. Spines 214 may have elliptical (e.g., circular) or rectangular (that may appear to be flat) cross-sections, and include a flexible, resilient material (e.g., a shape-memory alloy such as nickel-titanium, also known as Nitinol) forming a strut as will be described in greater detail herein.

As shown in FIG. 2A, the plurality of flexible linear spines 214 converge at a central spine intersection 211. In some examples central spine intersection 211 can include one or more cutouts 212 that allow for bending of the spines 214 when each spine respective attachment end 216 is connected to the spine retention hub 90, described in more detail below.

In embodiments described herein, one or more electrodes 40 positioned on spines 114 of basket assembly 38 can be configured to deliver ablation energy (RF and/or IRE) to tissue in heart 26. Additionally, or alternatively, the electrodes can also be used to determine the location of basket assembly 38 and/or to measure a physiological property such as local surface electrical potentials at respective locations on tissue in heart 26. The electrodes 40 can be biased such that a greater portion of the one or more electrodes 40 face outwardly from basket assembly 38 such that the one or more electrodes 40 deliver a greater amount of electrical energy outwardly away from the basket assembly 38 (i.e., toward the heart 26 tissue) than inwardly.

Examples of materials ideally suited for forming electrodes 40 include gold, platinum and palladium (and their respective alloys). These materials also have high thermal conductivity which allows the minimal heat generated on the tissue (i.e., by the ablation energy delivered to the tissue) to be conducted through the electrodes to the back side of the electrodes (i.e., the portions of the electrodes on the inner sides of the spines), and then to the blood pool in heart 26.

As shown in FIGS. 2A and 2B, basket assembly 38 has a distal end 39. The medical probe 22 can include a spine retention hub 90 that extends longitudinally from a distal end of tubular shaft 84 towards distal end 39 of basket assembly 38. As described supra, control console 24 includes irrigation module 60 that delivers irrigation fluid to basket assembly 38 through tubular shaft 84.

Figures 10A, 10B:
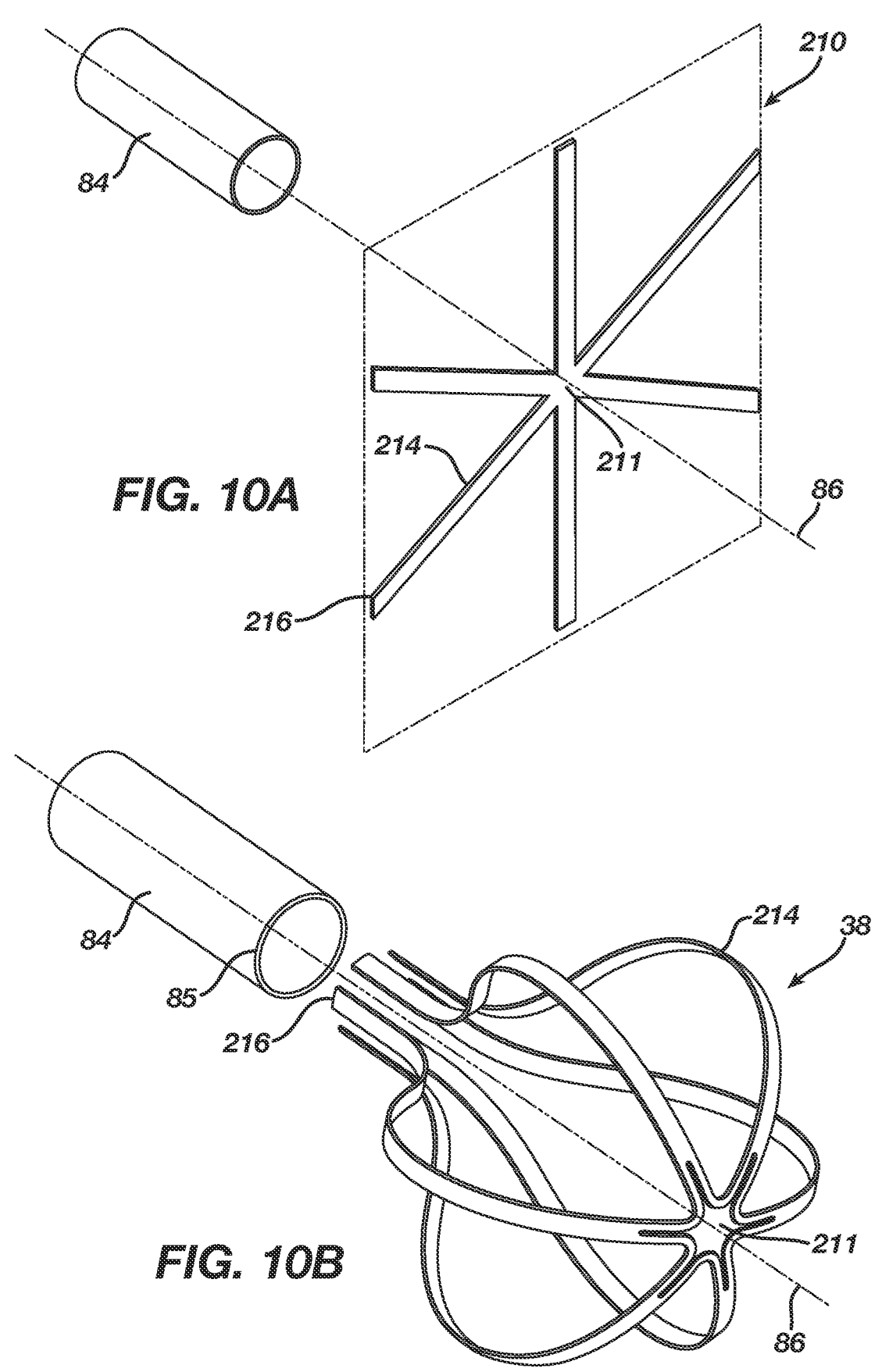
FIGS. 10A and 10B are schematic pictorial illustrations of a method of forming a basket assembly, in accordance with an embodiment of the present invention.

Turning to FIG. 2C, basket assembly 38 includes a single unitary structure that includes a plurality of spines 214 formed from a planar sheet of material 210 (shown more clearly in FIGS. 9 and 10A). The spine retention hub 90 can be inserted into the tubular shaft 84 and attached to the tubular shaft 84. Spine retention hub 90 can include a cylindrical member 94 including a plurality of relief lands 96, an irrigation hub 97, multiple irrigation openings 98, and at least one spine retention hub electrode 99, or some combination thereof. Relief lands 96 can be disposed on the outer surface of cylindrical member 94 and configured to allow a portion of each spine 214, such as each spine attachment end 216, to be fitted into a respective relief land 96. The attachment end 216 can be a generally linear end of the spine 214. The attachment end 216 can be configured to extend outwardly from the spine retention hub 90 such that the basket assembly 38 is positioned outwardly from the spine retention hub 90 and, consequently, outwardly from the tubular shaft 84. In this way, the spine 214 can be configured to position the basket assembly 38 distally from the distal end of the tubular shaft 84 and distal from the distal end of the insertion tube 30 when the basket assembly is deployed.

As described supra, control console 24 includes irrigation module 60 that delivers irrigation fluid to distal end 36. The multiple irrigation openings 98 can be angled to spray or otherwise disperse of the irrigation fluid to either a given electrode 40 or to tissue in heart 26. Since electrodes 40 do not include irrigation openings that deliver irrigation fluid, the configuration described hereinabove enables heat to be transferred from the tissue (i.e., during an ablation procedure) to the portion of the electrodes on the inner side of the spines 214, and the electrodes 40 can be cooled by aiming the irrigation fluid, via irrigation openings 98, at the portion of the electrodes 40 on the inner side of the spines 214. Spine retention hub electrode 99 disposed at a distal end of retention hub 90 can be used in combination with electrodes 40 on the spines 214, or alternatively, can be used independently from electrodes 40 for reference mapping or ablation.

Figure 2D:
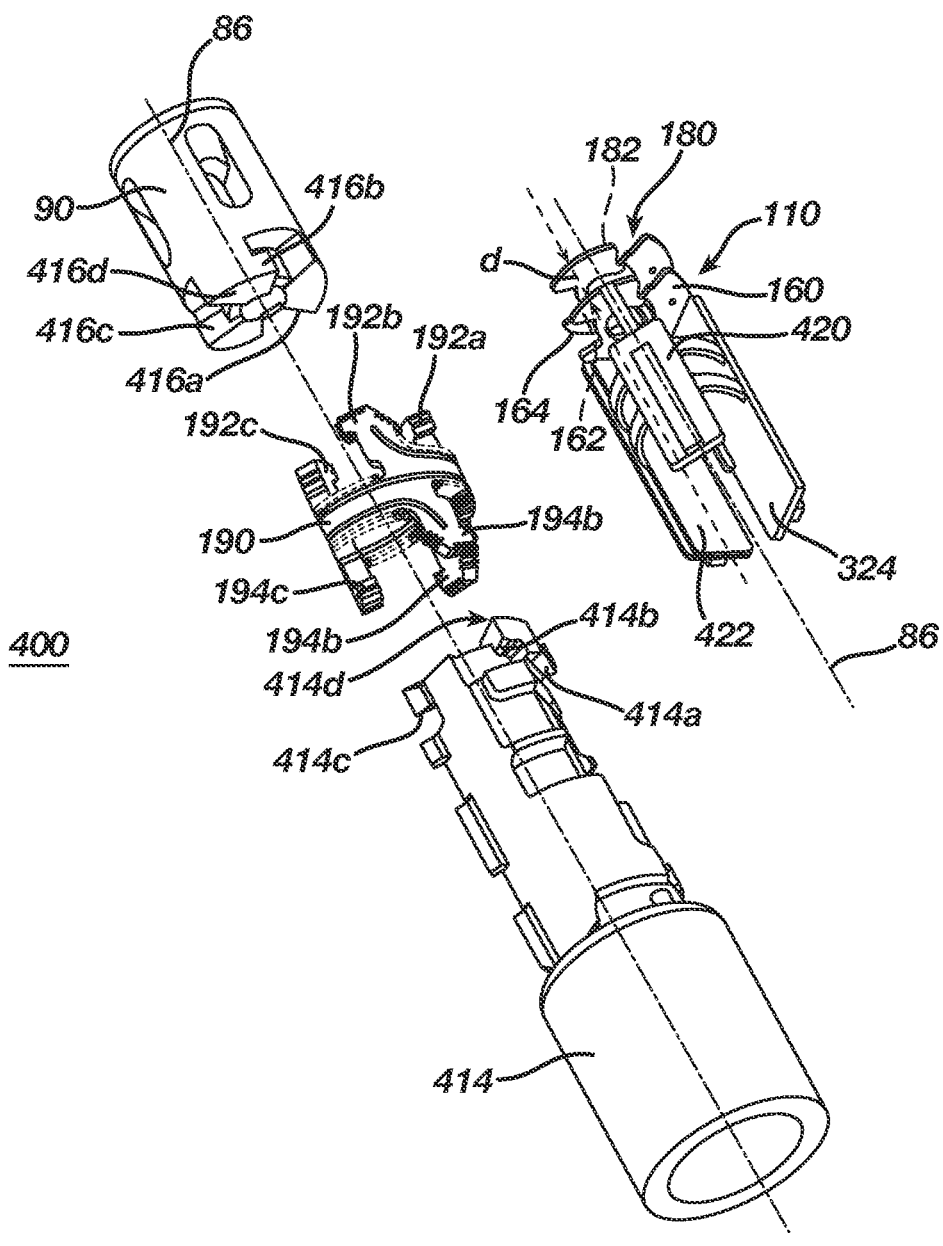
FIG. 2D is an exploded view of components for an example contact force sensor shown in FIG. 2C, in accordance with an embodiment of the present invention.

FIG. 2D is an exploded view for contact force sensor 400 referenced in FIG. 2C. As shown in FIG. 2D, the contact force sensor 400 is disposed inside tube 84 (not shown in FIG. 2D) and proximally in relation to the basket assembly 38 and as close as possible to the basket 38 so that contact with cardiac tissue by the spines 214 can be transmitted to the contact force sensor 400. Contact force sensor 400 includes coupler 414 provided with a plurality of notches 414a, 414b, 414c on the periphery of the cylindrical member or coupler 414 for corresponding engagement with protrusions 194a, 194b, 194c of beam coupling member 190. A spine retention hub or coupler 90 is provided with notches 416a, 416b, 416c that mate with protrusions 192a, 192b, 192*c* of beam coupling member 190. Flat surfaces 416*d* of spine retention hub or coupler 90 (angled with respect to axis 86 for spine retention hub or coupler 90) are formed whereby each flat surface 416*d* is angulated with respect to the axis 86 so that each flat surface is complementary to the angulation of beam coupling member 190 defined by the helicoid path of protrusions 194*a*, 194*b*, 194*c* (i.e., helix angle). Three flat surfaces (not shown due to the perspective view) 414*d* of contact force sensor 400 are also provided for coupler 414 in a configuration similar to flat surface 416*d* of spine retention hub or coupler 90 in that the three flat surfaces 414*d* are also angulated with respect to the axis 86 so that each flat surface 414*d* of coupler 414 are generally parallel to the angulation path of beam coupling member 190 defined by the helicoid ramp of protrusions 194*a*-194*c* as well as flat surface 416*d*.

The location sensor coils 422 and 424 are mounted to coupler 414 (for coupling with hub 96) in a generally equiangular configuration about the axis 86. It is noted that while two coils (for X and Y axes) are used in an exemplary embodiment to determine the location of these coils (as mounted to the coupler 414 and thereby the location of the basket spines as the distance between basket spines and the location sensor is known), in certain circumstances, only one location sensing coil may be utilized if the other two axes are known via other visualization techniques. As well, three location sensing coils may also be used depending on the packaging constraints of the catheter. Details of the contact force sensor are provided in U.S. Patent Application Publication No. 20210077180A1 published Mar. 18, 2021, which disclosure is incorporated by reference herein and attached in the appendix to priority application 63/323,807.

Figure 3A:
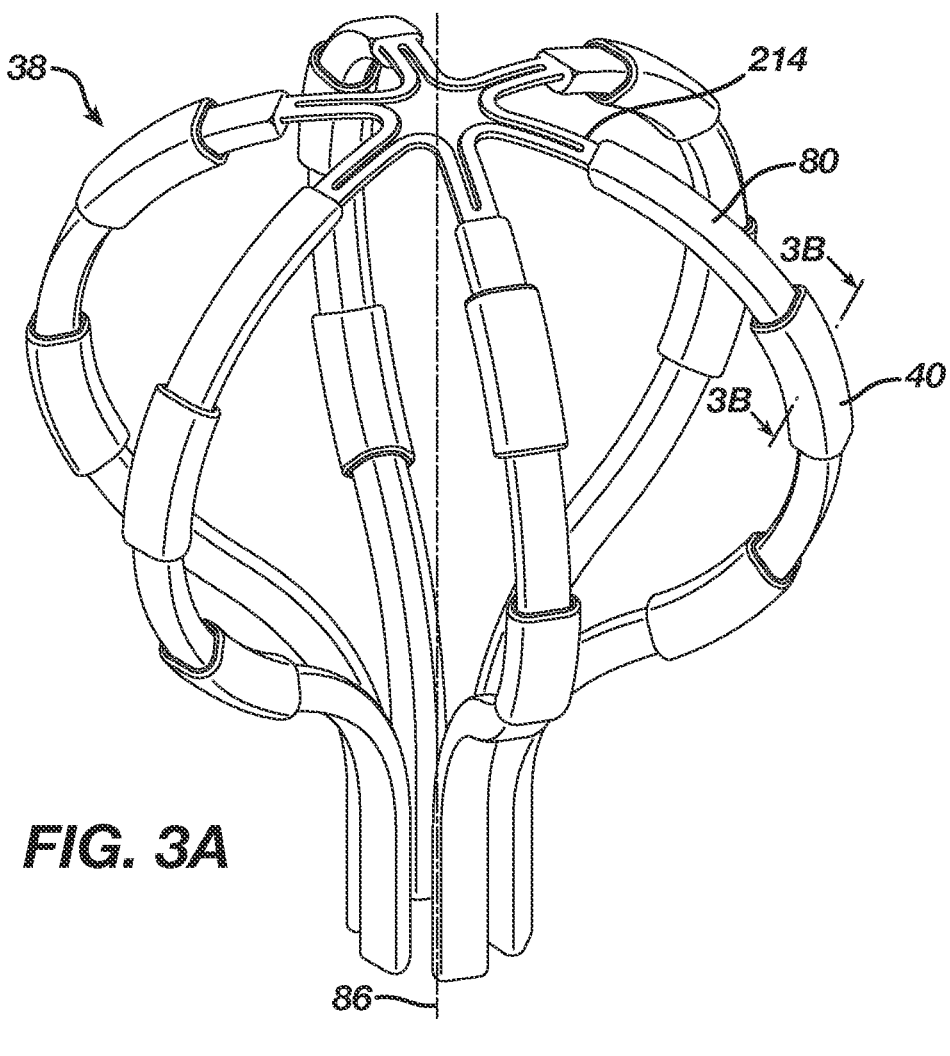
FIG. 3A is a perspective view of a medical probe in an expanded form, in accordance with an embodiment of the present invention.
Figure 3B:
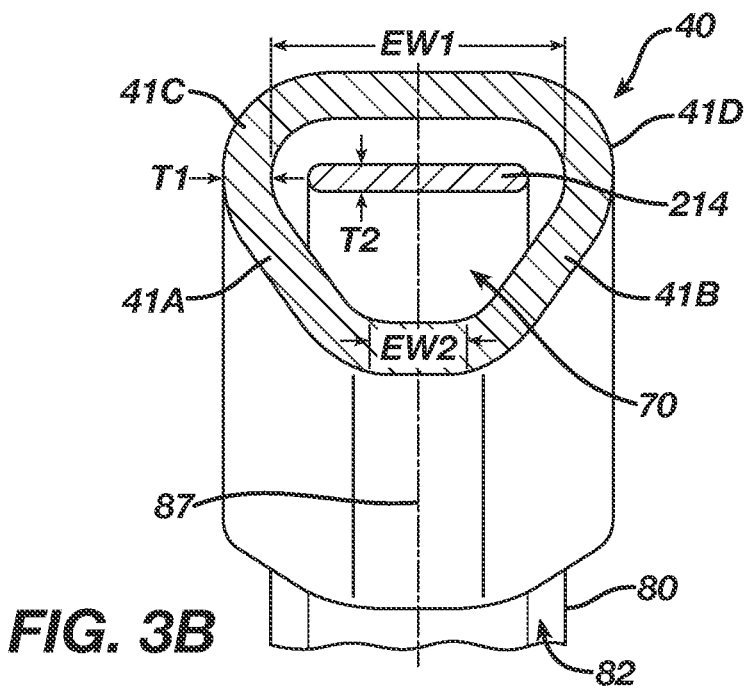
FIG. 3B illustrates a cross-sectional view of a respective spine, insulative jacket, and electrode of FIG. 3A, in accordance with an embodiment of the present invention.

FIG. 3A is a schematic pictorial illustration showing a perspective view of an expandable basket assembly in an expanded form when unconstrained and FIG. 3B illustrates a cross-sectional view of a respective spine 214, insulative jacket 80, and electrode 40 of FIG. 3A. As shown, a respective spine 214 can pass through the lumen 70 of the respective electrode 40 and the lumen 82 of the insulative jacket 80. Although not depicted, the lumen 70, 82 of the electrode 40 and insulative jacket 80 can provide sufficient room for a wire to pass through such that the electrode 40 can be in electrical communication with the control console 24, while also being electrically insulated from the spine 214. To this end, the insulative jacket 80 can include a first lumen 82 as shown here, or a second lumen further described in reference to FIGS. 5A and 5B.

As shown in FIG. 3B, the electrode 40 can include a first section 41A and a second section 41B, together defining a lengthwise direction of the electrode body. The two sections 41A, 41B can be inclined or tapered inward with respect to a central axis 87 of the electrode 40. As shown, the tapered two sections 41A, 41B can make up a first electrode width EW1 that is greater than a second electrode width EW2. The electrode can also include a portion having sections 41C, 41D that are substantially parallel and forming a rectangular portion with respect to the first electrode width EW1 prior to the two sections 41A, 41B tapering to form the second electrode width EW2, forming a substantially trapezoidal cross-sectional shape, as more clearly depicted in FIG. 4A. The proportion of the tapered sections 41A, 41B to parallel sections 41C, 41D can vary for various applications, size of the respective spine 214 or insulative jacket 80 passing through the lumen 70 of the respective electrode 40.

Figures 5A, 5B, 5C:
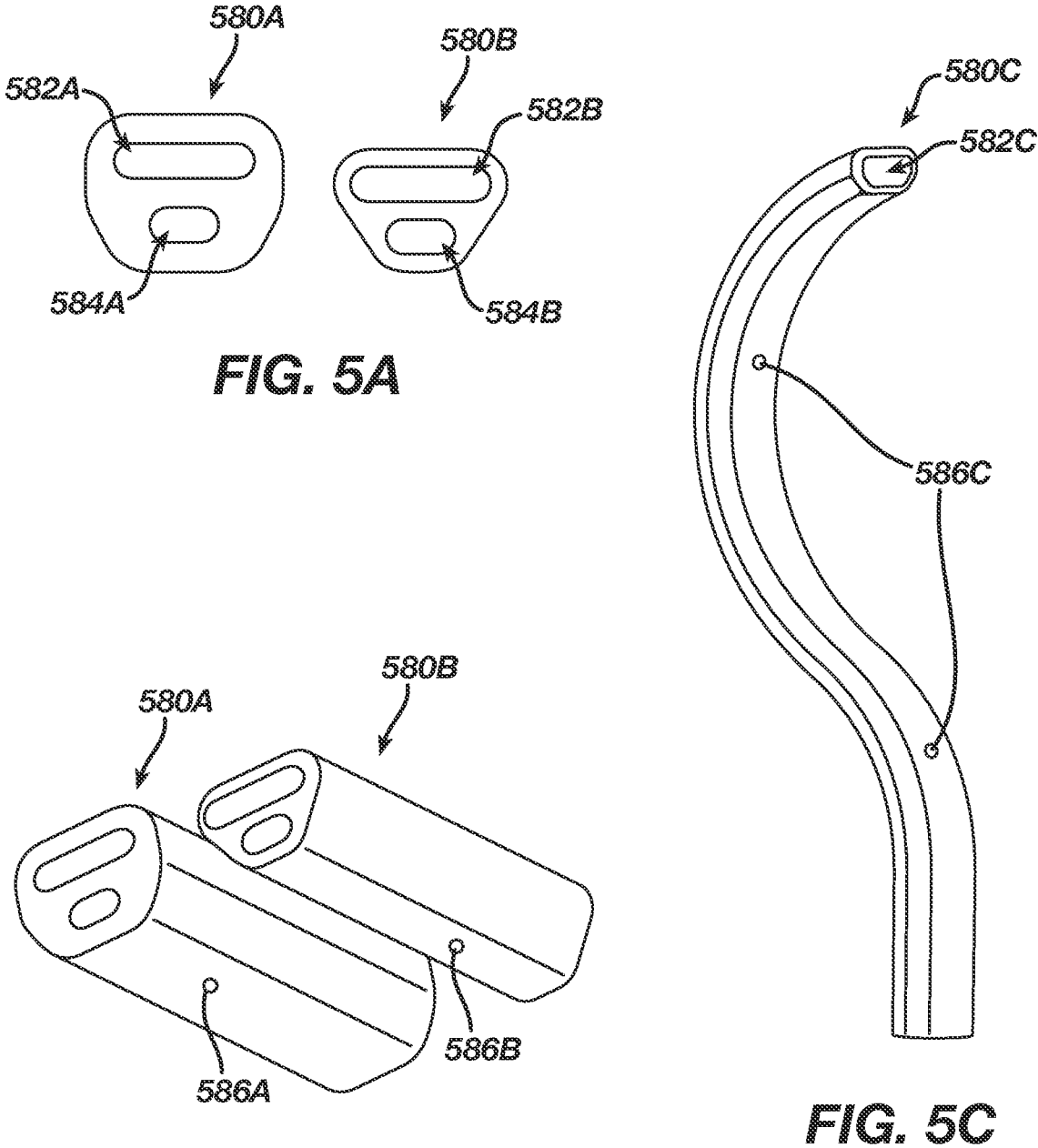
FIGS. 5A-5C are schematic pictorial illustrations showing various insulative jackets of a given medical device, in accordance with embodiments of the present invention.

In some examples, the electrode 40 can include a cross-sectional thickness T1 that is substantially similar to a cross-sectional thickness T2 of the respective spine 214. The cross-sectional thickness of the electrode 40 can allow each electrode body to bow radially outward from the central axis 87 of the respective electrode, as illustrated in FIG. 5B. Having a cross-sectional thickness that allows for the electrode 40 to bow or curve with the respective spine 114 allows the basket assembly 22 to transition from a collapsed form to an expanded form along the longitudinal axis 86 more effectively. In some examples, the plurality of spines 214 can have a cross-sectional thickness of about 0.05 mm (0.002") to about 0.15 mm (0.006") Each electrode body 40 can have a wall cross-sectional thickness "t" of about 0.03 mm (0.001") to about 0.13 mm (0.005"). Each electrode body 40 can have a wall cross-sectional thickness of about 0.1 mm (0.004") to about 0.3 mm (0.012").

Referring back to FIG. 2A through FIG. 2C, one or more electrodes 40 can be attached to spines 214 to form the basket assembly 38. In some examples, each electrode 40 can include electrically conductive material (e.g., gold, platinum and palladium (and their respective alloys)). Alternatively, or in addition thereto, the electrode 40 can include precious metal or nitinol. When including nitinol, the electrode may be shape set with a desired contour. In addition, electrodes may be laser-cut from hypodermic tubing having a round or trapezoidal shape to facilitate flex, or from hypodermic sheet metal.

Turning to FIGS. 4A through 4F, electrode 40 can have a variety of cross-sectional shapes, curvatures, lengths, lumen number and lumen shape. The electrode 440 (or 440') is offered to illustrate one various configuration of electrodes 40 that can be used with the medical device 22 but should not be construed as limiting. One skilled in the art will appreciate that various other configurations of electrodes 40 can be used with the disclosed technology without departing from the scope of this disclosure.

Each electrode 440 can have an outer surface 474 facing outwardly from electrode 440 and an inner surface 476 facing inwardly toward electrode 440 where at least one lumen 470 is formed through electrode 440. The lumen 470 can be sized and configured to receive a spine 214 such that spine 214 can pass through electrode 440. Lumen 470 can be a symmetric opening through electrode 440 and can be disposed offset with respect to a central axis 87 of the respective electrode. In other examples, lumen 470 can pass through electrode 440 in a generally transverse direction with respect to the central axis 87 of the respective electrode. Furthermore, lumen 470 can be positioned in electrode 440 nearer a bottom surface, nearer a top surface, or nearer a middle of electrode 440 depending on the particular configuration. In FIGS. 4A and 4B, the top surface (upper side) is oriented toward the top of the drawing, the bottom surface (lower side) is oriented toward the bottom of the drawing, and the middle is between the top surface and the bottom surface. In other words, each electrode 440 can include a lumen 470 that is offset with respect to a centroid of the electrode 440.

In addition, as shown in FIGS. 4A through 4F, electrodes 440 can have a lumen 470 large enough for a respective spine 214 and a wire to pass through the electrode such that the electrode 440 can be in electrical communication with the control console 24. Although not shown, electrodes 440 can also include a wire relief forming a recess or depression in electrode 440 adjacent lumen 470 for one or more wires to pass through lumen 470 along with a respective spine 214. Relief can be sized to provide room for a wire of electrode 440 to pass through electrode 440 such that electrode 440 can be in electrical communication with the control console 24.

Alternatively, or in addition thereto, wires can pass through a wire lumen. Although not depicted, electrodes 40 may include both a wire relief adjacent lumen 470 and wire lumen. Such electrode may permit additional wires to pass through the electrode body.

As shown in FIGS. 4A-4F, the electrodes 440 can include a cross-sectional shape that is substantially trapezoidal. In particular, electrodes 440 can include two sections 441A, 441B that define a lengthwise direction of the electrode 440. The two sections 441A, 441B can be inclined inward with respect to the central axis 87 of the respective electrode 440. Although not illustrated, the two sections 441A, 441B can be of various lengths such that the dimensions of the substantially rectangular portion having the first electrode width EW1 can be either greater than the dimensions of the inwardly inclined portion having the second electrode width EW2 as shown described in FIG. 3B supra.

Figure 4E:
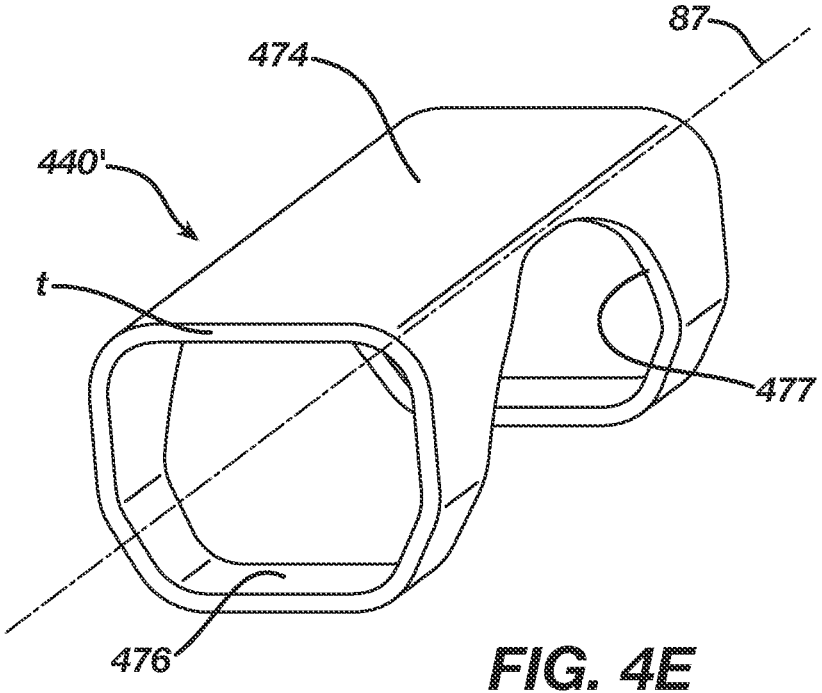
Figure 4F:
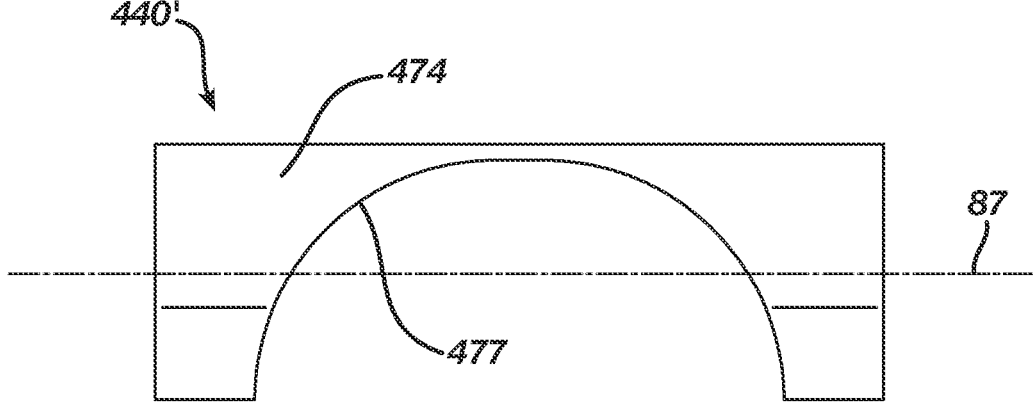

In FIGS. 4E and 4F, the electrode 440' is a variation of electrode 440 in which electrode 440' is not required to have a curved shape due to the inclusion of a cut-out 477 to allow for bending of the electrode 440' along its longitudinal axis 87. Cut out 477 is shown in FIG. 4F as being semi-circular but any other shapes can be utilized as long as such cutout allows for bending of the electrodes when the spine (on which the electrode 440' is mounted) is expanded into the basket shape configuration.

FIGS. 5A through 5C are schematic pictorial illustrations showing various insulative jackets 580A-580C of a given medical device 22, in accordance with embodiments of the present invention. FIG. 5A is a front view while FIGS. 5B and 5C are perspective views of insulative jackets 580A-80C. Insulative jackets 580A-580C can be made from a biocompatible, electrically insulative material such as polyamide-polyether (Pebax) copolymers, polyethylene terephthalate (PET), urethanes, polyimide, parylene, silicone. In some examples, insulative material can include biocompatible polymers including, without limitation, polyetheretherketone (PEEK), polyglycolic acid (PGA), poly(lactic-co-glycolic acid) copolymer (PLGA), polycaprolactive (PCL), poly(3-hydroxybutyrate-co-3-hydroxyvalerate) (PHBV), poly-L-lactide, polydioxanone, polycarbonates, and polyanhydrides with the ratio of certain polymers being selected to control the degree of inflammatory response. Insulative jackets 580A-580C may also include one or more additives or fillers, such as, for example, polytetrafluoroethylene (PTFE), boron nitride, silicon nitride, silicon carbide, aluminum oxide, aluminum nitride, zinc oxide, and the like. Insulative jacket 580A-580C can help to insulate a spine 214 and/or wires passing through insulative jacket 580A-580C from electrode 40 to prevent arcing from electrode 40 to the spine 214 and/or mechanical abrasion of wires passing through insulative jacket 580A-580C.

As illustrated in FIGS. 5A through 5C, insulative jackets 580A-580C, can include a cross-sectional shape that is substantially trapezoidal. The insulative jacket may consist of a single lumen (as shown in FIG. 5C) or multi-lumen configuration (depicted in FIGS. 5A and 5B). Multi-lumen jackets may be configured such that the alloy frame and wires share a single lumen while the second lumen may be used for irrigation. The alloy frame and wires may occupy separate lumens, also, as described. The current embodiment does not utilize irrigated jackets. For these designs, the insulative jackets may be continuous (individual sleeves extending from proximal to distal end of each alloy frame strut), segmented (bridging between electrode gaps), or a combination of both. Furthermore, insulative jacket 580A, 580B can include a first lumen 582A, 582B and a second lumen 584A, 584B, while insulative jacket 580C includes only a first lumen 582C. In one configuration, first lumen 582A, 582B can be configured to receive spine 214 while second lumen 584A, 584B can be configured to receive a wire, or vice-versa. In other examples, first lumen 582A-582C can each be configured to receive spine 214 in addition to one or more wires that can be connected to one or more electrodes 40. Furthermore, as illustrated in FIGS. 5B and 5C, insulative jacket 580A-580C can include an aperture 586A-586C through which a wire can be electrically connected to electrode 40. Although illustrated in FIGS. 5B and 5C as being proximate a bottom of insulative jacket 580A-580C, aperture 586A-586C can be positioned proximate a top or side of insulative jacket 580A-580C. Furthermore, as shown in FIG. 5C, insulative jacket 580A-580C can include multiple apertures 586A-586C with each aperture being disposed on the same side of insulative jacket (i.e., top, bottom, left, right) or on different sides of the insulative jacket depending on the application.

Figures 6A, 6B, 7A:
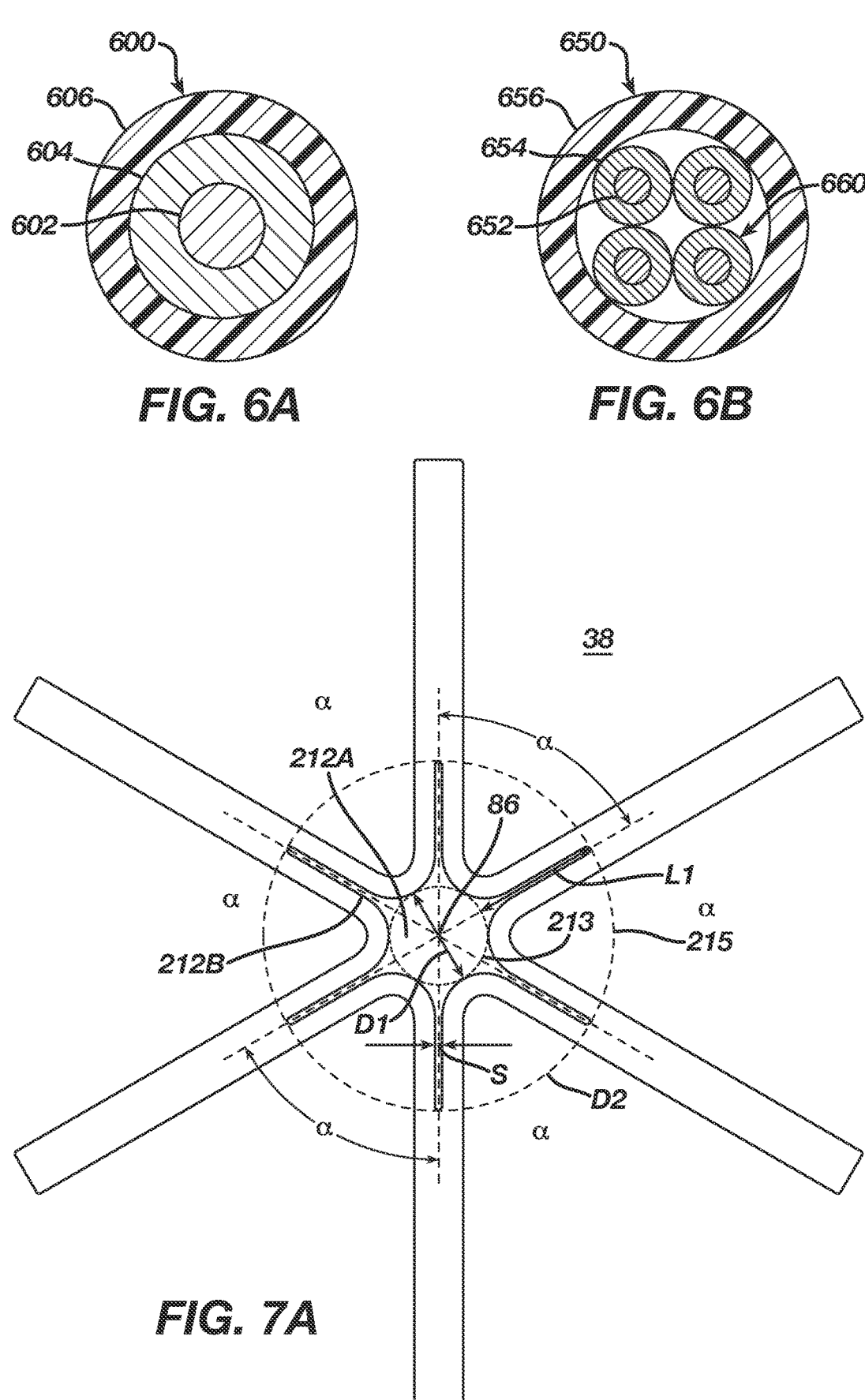
FIGS. 6A and 6B are schematic pictorial illustrations showing cross-sectional views of a given wire of a medical probe, in accordance with an embodiment of the present invention.
FIGS. 7A through 7E are schematic pictorial illustrations of central spine intersections, in accordance with an embodiment of the present invention.

FIGS. 6A and 6B are schematic pictorial illustrations showing cross-sectional views of a given wire 600, 650 that can be connected to a given electrode 40, in accordance with an embodiment of the present invention. FIG. 6A illustrates a solid core wire 600. FIG. 6B illustrates a stranded wire 650. Each wire 600, 650 can extend through at least a portion of tubular shaft 84 and tubular shaft 84. Solid core wire 600 can include an electrically conductive core material 602 and an electrically conductive cover material 604 circumscribing electrically conductive core material 602. Likewise, stranded wire 650 can include strands each including an electrically conductive core material 652 and an electrically conductive cover material 654 circumscribing the electrically conductive core material 652. Each wire 600, 650 can include an insulative jacket 606 circumscribing the conductors. The wires 600, 650 can be configured to withstand a voltage difference of adjacent wires sufficient to deliver IRE pulses. Preferably, the wires 600, 650 can withstand at least 900V, and more preferably at least 1,800V between adjacent wires. To reduce likelihood of dielectric breakdown between conductors of adjacent wires, electrically conductive cover material 604, 654 can have a lower electrical conductivity compared to core material 602, 652.

Insulative jacket 606 can be configured to have a temperature rating between 150 and 200 degrees Centigrade so that the electrically insulative jacket 606 melts or degrades (e.g., chars and crumbles) during soldering of wire 600 to electrodes 40 (e.g., at a temperature of 300 degrees Centigrade) and therefore insulative jacket 606 of wire 600 does not need to be mechanically stripped. In other examples, insulative jacket 606 can have a temperature rating greater than 200 degrees Centigrade to prevent electrically insulating material 602 melting or degrading (e.g., charring and crumbling) during manufacture of medical probe 22 and/or during use. Insulative jacket 606 can be mechanically stripped from wire 600 prior to wires 600 being electrically connected to electrodes 40.

Figure 7B:
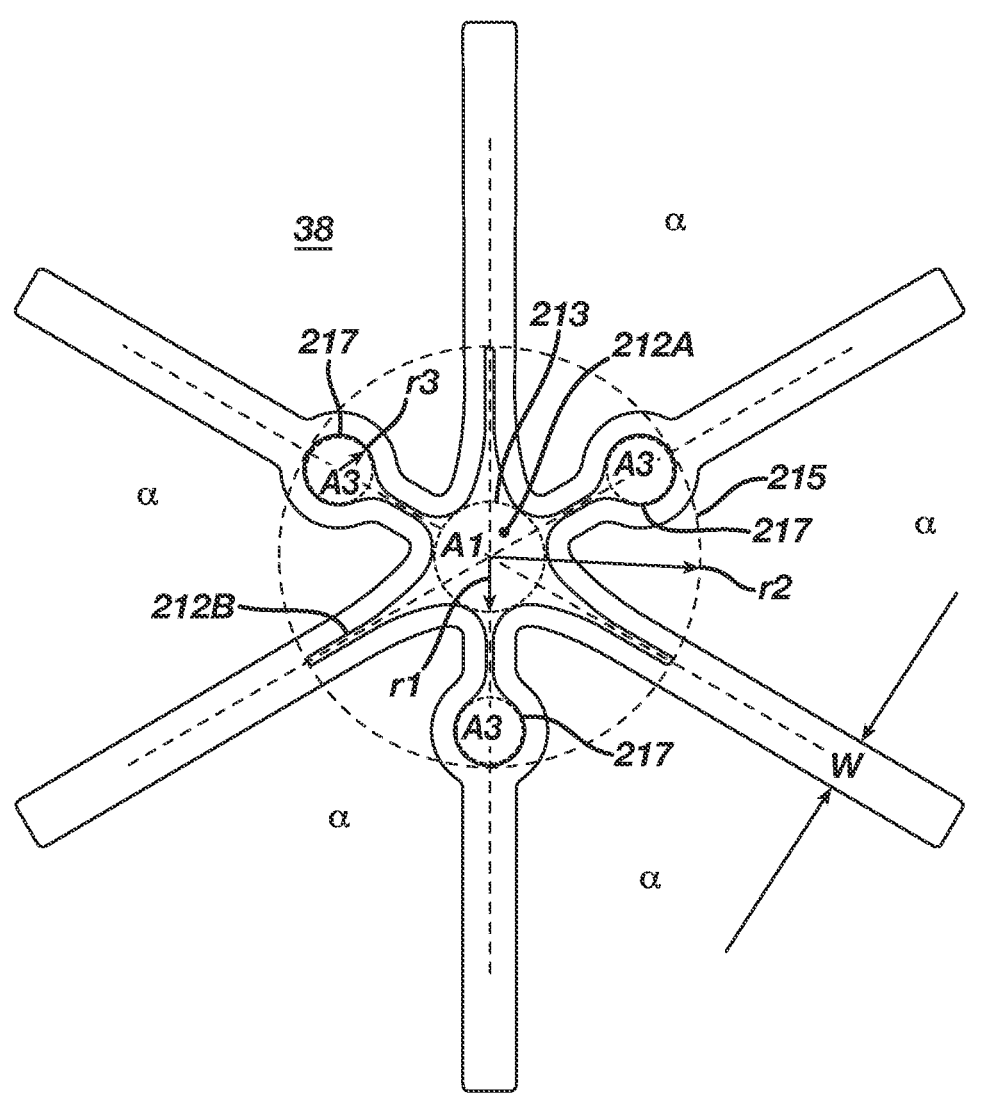

FIGS. 7A through 7E are schematic pictorial illustrations of top-down views of basket assembly 38, showing various examples of one or more cutouts 212 on central spine intersection 211. As shown, intersection 211 can include a single discrete cutout 212A, as shown in FIGS. 7A and 7B. Alternatively, intersection 211 can include two or more cutouts 212B, as provided as an example in FIGS. 7C and 7D. The one or more cutouts 212A, 212B can include a variety of patterns, such as centrosymmetric (i.e., symmetric with respect to a central point), and equiangular (i.e., including equal angles) to allow for equal bending among the spines 214 as well as disproportional and asymmetric to allow for unequal bending of spines 214 to alter structural stability. In certain instances, when basket assembly 38 includes an even number of spines 214, the pattern of the one or more cutouts 212 can alter between every other spine, as illustrated in FIG. 7B. In some examples, one or more cutouts 212 can extend along a portion of each spine 214. Each of the designs illustrated in FIGS. 7A-7E will be discussed separately.

In FIG. 7A, the distal end of the basket assembly 38 has an open cutout 212 which is a combination of a central opening 212A (substantially approximated by a virtual circle 213 with diameter D1) and the groove 212B for each spine (giving a total of six grooves 212B). Each spine is disposed generally equiangularly about the longitudinal axis of a predetermined angle α between any two spines. Each groove 212B has groove width S that extend approximately a length L1 from the circumference of virtual circle D1 so that a virtual circle 215 with diameter D2 is contiguous to the grooves 212B. The second virtual circle 215 has a diameter D2 approximately 3.6 times that of the diameter D1 of the first virtual circle 213. In one embodiment, the cutout 212 (represented by center cutout 212A and open grooves 212B) has a negative area of about 1.9 mm-squared with the diameter of the virtual circle 213 of about 1.1 mm and the virtual circle 215 of about 4 mm such that each open groove 212B has a width S of about 0.08 mm extending for about 1.5 mm from the virtual circle 213 so that the negative area defined by all the cutouts in this design includes approximately 1.9 mm-squared.

In FIG. 7B, the basket 38 has its distal portion configured to have an open center 212A that radiates into each of the six spines 214. The open center 212A has a first area A1 that can be approximated by a virtual circle with radius r1. Three spines approximately 120 degrees apart have tapering grooves 212B extending back toward the proximal portion of basket 38. Three other spines approximately 120 degrees apart have large apertures 217 with area A3 disposed towards the proximal portion of the basket 38. The cutout area A3 can be approximated by a virtual circle with radius r3 and disposed on the spines 214 such that the apertures 217 are contiguous to the inside circumference of virtual circle 215 with radius r2. In this configuration, each third area A3 is about ¼ of the open first area A1 while the total negative surface area of the entire cutout includes approximately 1.6 times the first open area of empty space A1 and the second area A2 (calculated with radius r2) includes approximately 7 times the first area A1. Additionally, the second area A2 includes approximately 36 times third area A3. The radius r3 includes approximately 0.4 times that of radius r1 while radius r2 includes approximately 2.8 times that of radius r1. In one exemplary embodiment, first open area of empty space A1 includes approximately 2 mm-squared; second area A2 (as defined by radius r2) being approximately 15 mm-squared; third area A3 includes approximately 0.4 mm-squared; total area of all cutouts includes approximately 3.5 mm-squared; radius r1~0.8 mm; r2~2.2 mm; and r3~0.4 mm.

Figure 7C:
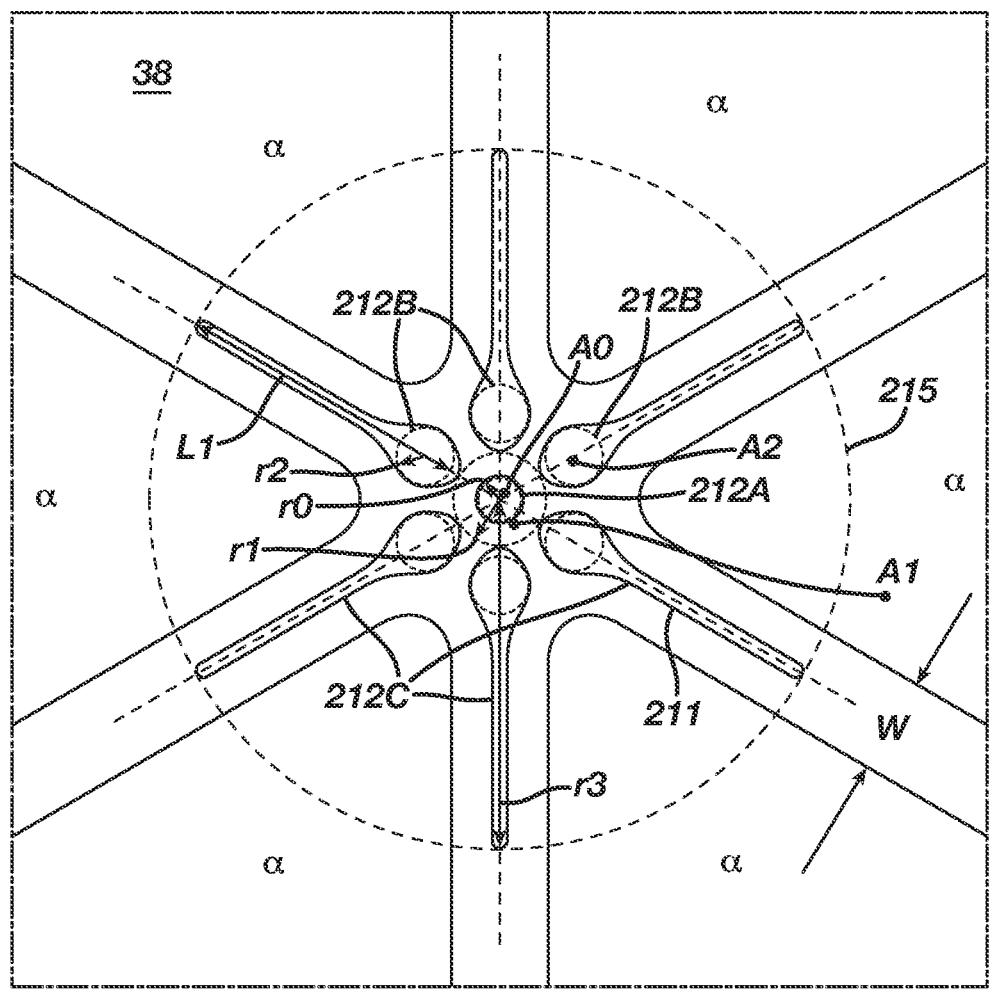

In FIG. 7C, this design has a small aperture 212A disposed at the center (coincident with longitudinal axis 86) of the basket 38 with a tadpole shaped cutout 211 disposed on each of the spines 214. Each tadpole cutout 211 is defined by an aperture cutout 212B that is merged with grooved cutout 212C. It is noted that while aperture 212A or 212B is shown approximating the of a circle, it is within the scope of this invention to have cutout opening 212A or 212B in any shape as long as each aperture 212A or 212B has the requisite negative area. In the event the aperture 212A is configured as a circle, aperture 212A has central void A0 (of negative area) that can be approximated by a first virtual circle with radius r0 while each aperture 212B has a second area A2 that can be represented by a second virtual circle with radius r2. The apertures 212B (or the "heads" of the tadpole cutouts) are radially arrayed so that apertures 212B are contiguous to a first virtual circle with radius r1. The second virtual circle may have a second radius r2 of 1.2 times that of the radius r0 of the first virtual circle representing aperture 212A while the first virtual circle r1 may have radius r1 of approximately 1.5 times that of the radius of the central virtual circle r0. The tail or grooved opening 212C of the "tails" extends towards the proximal end of the basket 38 for a length L1 so that each tail is contiguous to an inside circumference of a third virtual circle 215. Slot length L1 includes approximately 6-10 times that of the first radius r1. Third virtual circle 215 may have a radius r3 extending from the longitudinal axis 86 where radius r3 includes approximately 10-15 times that of either first radius r1 or central radius r0. In the exemplary embodiment (amongst many), the negative area of each of the tadpole cutout 211 includes approximately 0.2 mm-squared while the negative area of center aperture 212A includes approximately 0.05 mm-squared so that the total negative area defined by all of the cutouts includes approximately 1.4 mm-squared. In the same exemplary embodiment, the central radius r0 may be approximately 0.13 mm, the second radius r2 may be approximately 0.2 mm, and the first radius r1 may be approximately 0.23 mm.

Figure 7D:
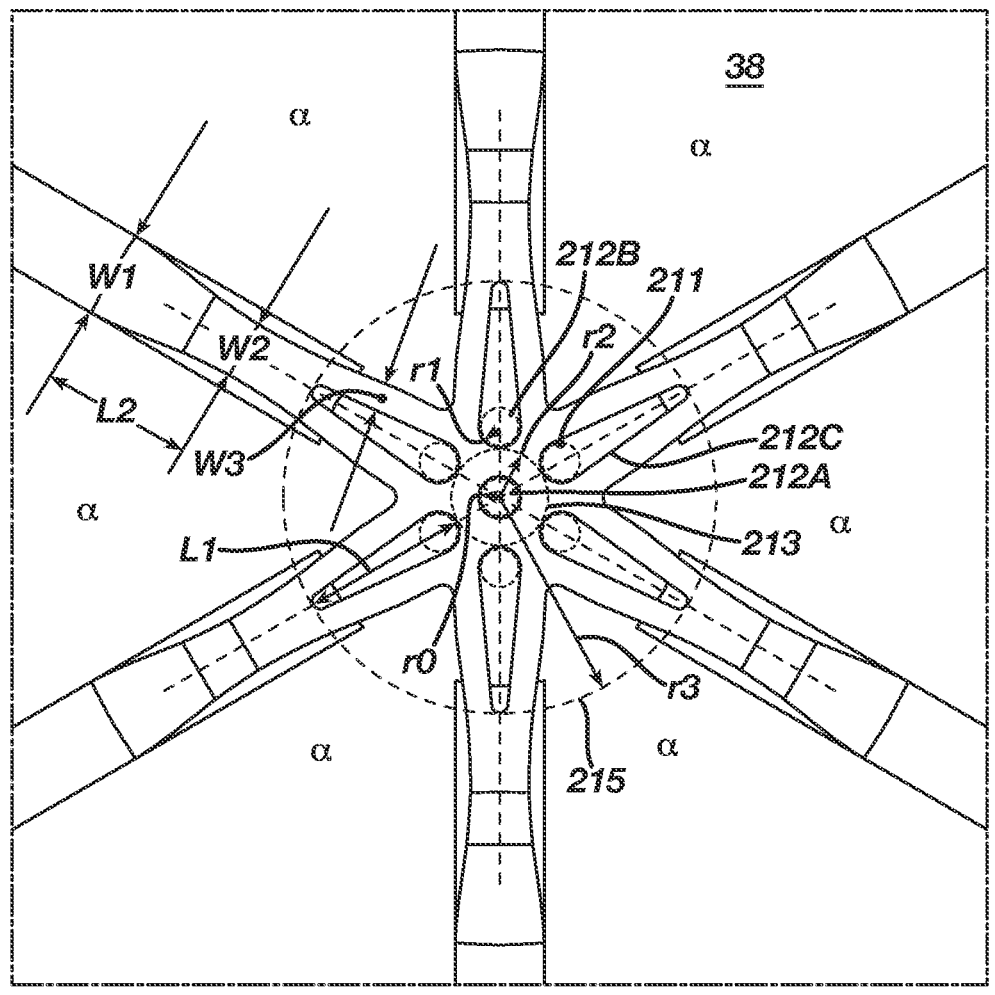

In FIG. 7D, the design of the basket 38 is provided with an aperture 212A at approximate center (i.e., axis 86) of the spines 214. Each spine 214 is provided a comet-shaped cutout 211 with head portion 212B with an open tapered slot tail 212C tapering towards the proximal portion of each spine 214. The comet-shaped cutouts 212B are arrayed so that the distal head portion 212B of the cutout 211 are contiguous to an outside circumference of second virtual circle 213 while the proximal slotted opening 212C of the cutouts 211 are contiguous on the inside circumference of third virtual circle 215. Where the aperture 212A is configured as a circular hole located on central axis 86 with radius r0 where the first radius r1 includes approximately 90% of the central radius r0, the second virtual circle 213 may have a second radius r2 of approximately 2.5 times that of central radius r0 while the third virtual circle 215 has a radius r3 of approximately 10 times that of the central radius r0 (all measured from center axis 86). Spine 214 has a first width W1 that tapers towards central axis 86 to a narrower second spine width W2 of approximately 66% of first spine width W1 at its narrowest point before being sub-divided by comet shaped cutout 212B into two narrower spine arms with each arm including a third spine width W3 of approximately ⅓ that of the width W1. The comet shaped cutout 212B has a length L1 along the spine of approximately 1.8 times that of the largest spine width W1.

Figure 7E:
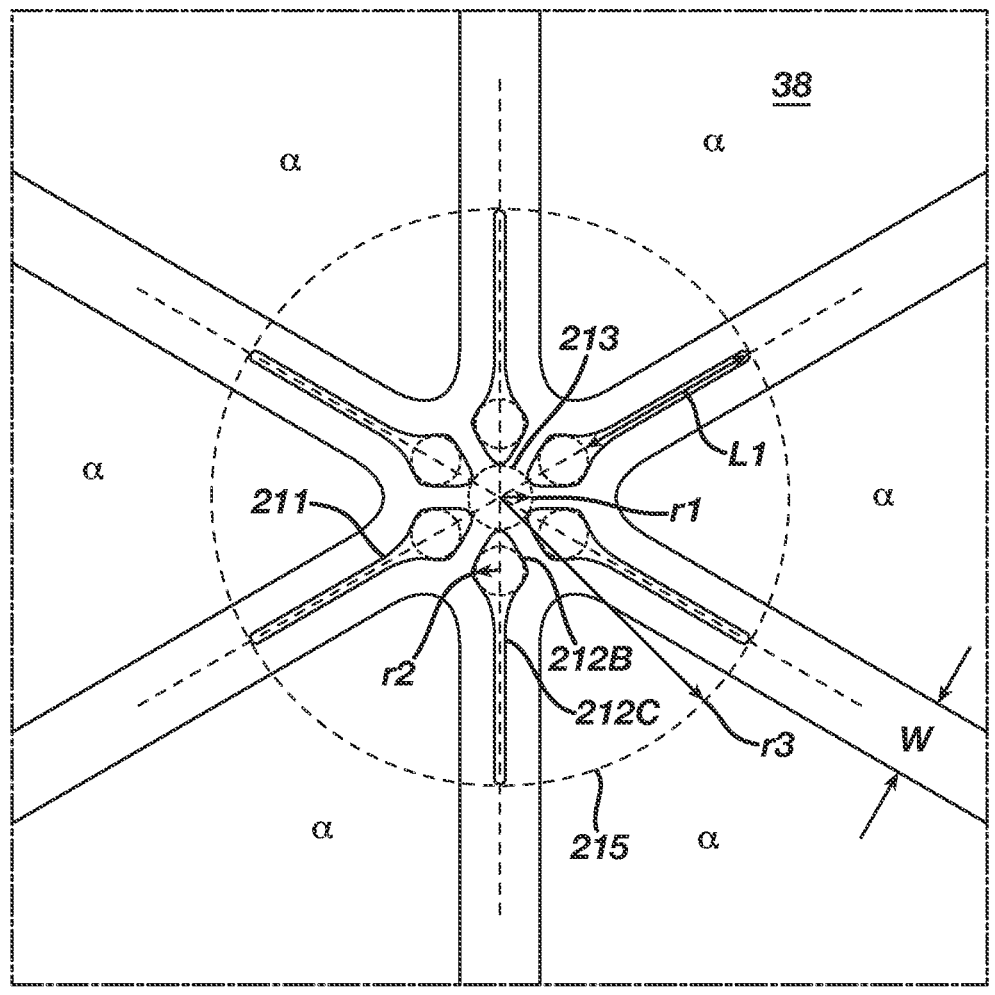

In FIG. 7E, the center (on longitudinal axis 86) of the radiating spines 214 for basket 38 does not have a cutout so that there is no void at the center of the basket to act as sharp edge surface (at the edge of such center aperture) against biological tissues. To allow for consistent folding of the spines near the distal portion of basket 38, each spine is provided with a tadpole shaped cutout 211 that extends from the head portion 212B to tail portion 212C. The head portions 212B are arrayed so that the head portions 212B are contiguous to an outside circumference of first virtual circle 213 with radius r1. Each head portion 212B has a negative surface area that can be approximated by a second virtual circle with radius r2 of approximately 90% of the first radius r1. The tail portions 212C are bounded by a third virtual circle 215 with a radius r3 approximately 10 times that of the first radius. The length L1 of each of the tail portion includes approximately 1.5 times that of the width W1 of the spine 214. In one exemplary embodiment (out of many), the total negative area of the six cutouts includes approximately 1.5 mm-squared.

The spines 214 can be folded or otherwise bent such that each respective attachment end 216 of the spine 214 can be inserted into the distal end 85 of the tubular shaft 84 (as shown in FIG. 2B) and relief lands 96 of spine retention hub 90 (not shown). Although not shown in FIGS. 10A and 10B, it will be appreciated that electrodes 40 can be attached to spines 214 before the spines are inserted into the tubular shaft 84 to form the basket assembly 38. As stated previously, the spines 214 can include a flexible, resilient material (e.g., a shape-memory alloy such as nickel-titanium, also known as Nitinol) that can enable the basket assembly 38 to transition to its expanded form (as shown in FIG. 2A) when the basket assembly 38 is deployed from tubular shaft 84. As will become apparent throughout this disclosure, spines 214 can be electrically isolated from electrode 40 to prevent arcing from electrode 40 to the respective spine 214.

As will be appreciated by one skilled in the art with the benefit of this disclosure, basket assembly 38 shown in FIGS. 2A through 2C including spines 214 formed from a single sheet of planar material and converging at a central intersection is offered merely for illustrative purposes and the disclosed technology can be applicable to other configurations of basket assemblies 38. For example, the described configuration of the basket spine assemblies can be obtained via laser cutting a nitinol tube and heat treating the spines from the tubular stock into substantially the planar form shown herein. As well, the disclosed technology can be applicable to basket assemblies 38 formed from a single spine 214 or multiple spines 214 with each spine 214 being attached at both ends. In other examples, the basket assembly 38 can include a central hub connecting the multiple spines 214 together at a distal end 39 of the basket assembly 38. In yet other examples, the basket assembly 38 can include a single spine 214 configured to form a spiral, multiple spines 214 configured to form a spiral, multiple spines 214 configured to form a tripod or multiple tripods, or any other shape of basket assembly 38. Thus, although FIGS. 2A through 2C illustrate a specific configuration of basket assembly 38, the disclosed technology should not be construed as so limited.

In the exemplary embodiments shown herein, the spines width W may have a nominal width of approximately 0.6 mm and can be as low as 0.2 mm or as large as 1.5 mm. The thickness of each spine can be nominally 0.09 mm and can vary from 0.05 mm to 0.2 mm. It should be noted that these values for width and thickness can vary depending on the stiffness desired.

FIGS. 8A and 8B are schematic pictorial illustrations showing a profile outline of a basket assembly 38A, 38B such that when the basket assembly is deployed the spines define a three-dimensional shape including the profile. The basket assembly can be approximately spheroid including an approximately circular profile as shown in FIG. 8A. The basket assembly can have an approximately oblate-spheroid shape including an approximately elliptical profile as shown in FIG. 8B. Although not every variation of shape is shown or described herein, one skilled in the art will appreciate that spines 214 can be further configured to form other various shapes as would be suitable for the particular application.

By including spines 214 configured to form various shapes when in the expanded form, basket assembly 38 can be configured to position the various electrodes 40 attached to spines 214 at various locations, with each location being nearer or farther from the distal end of tubular shaft 84. For example, electrode 40 attached to spine 214 illustrated in FIG. 8A near the middle of spine 214 would be farther from the distal end of tubular shaft 84 than spine 214 illustrated in FIG. 8B when basket assembly 38 is in the expanded form. In addition, each spine 214 may have an elliptical (e.g., circular) or rectangular (that may appear to be flat) cross-section, and include a flexible, resilient material (e.g., a shape-memory alloy such as nickel-titanium (also known as Nitinol), cobalt chromium, or any other suitable material).

FIGS. 9, 10A and 10B are schematic pictorial illustrations showing views of spines 214 forming basket assembly 38. FIG. 9 provides one example of how planar sheet of material 210 may be assembled together with tubular shaft 84 whereby each spine 214 bends or curves when respective attachment ends 216 are connect to spine retention hub 90. As shown in FIG. 10A, the spines 214 can be formed from a single sheet of planar material 210 to form a generally star shape. In other words, spines 214 can be formed from the single sheet of planar material such that the spines 214 converge toward a central intersection 211. The intersection 211 can be a solid piece of material (as shown in FIG. 10A) or include one or more cutouts 212 (as shown in FIG. 10B). Basket assembly 38 can include a number of spines 214 ranging from about four to about ten spines from a single sheet of planar material 210.

Figure 10C:
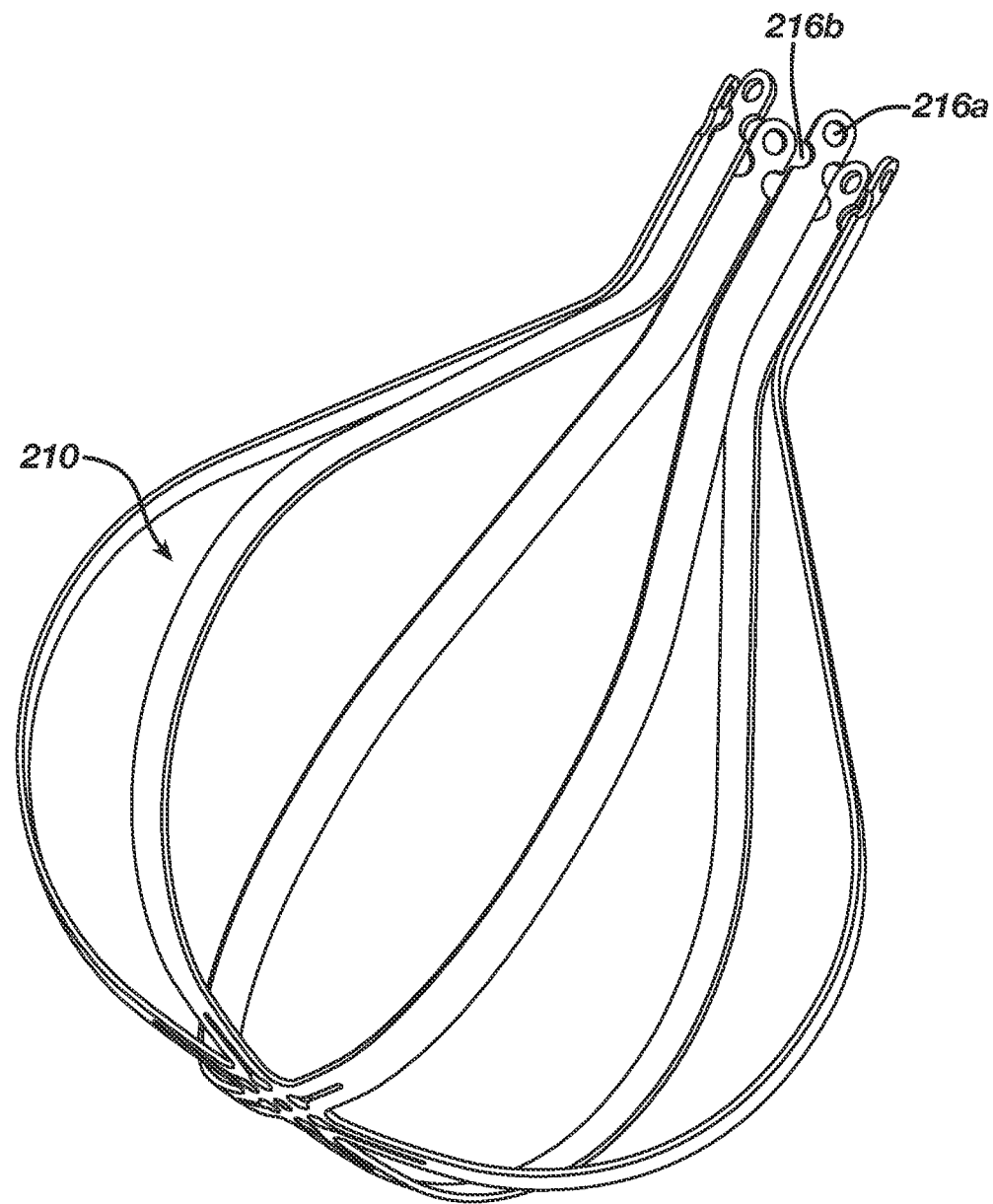
FIG. 10C illustrates an embodiment where the proximal end of each spine is provided with a hole and reference notches to ensure correct alignment and retention of the spine to the irrigation tube, in accordance with an embodiment of the present invention.
Figure 10D:
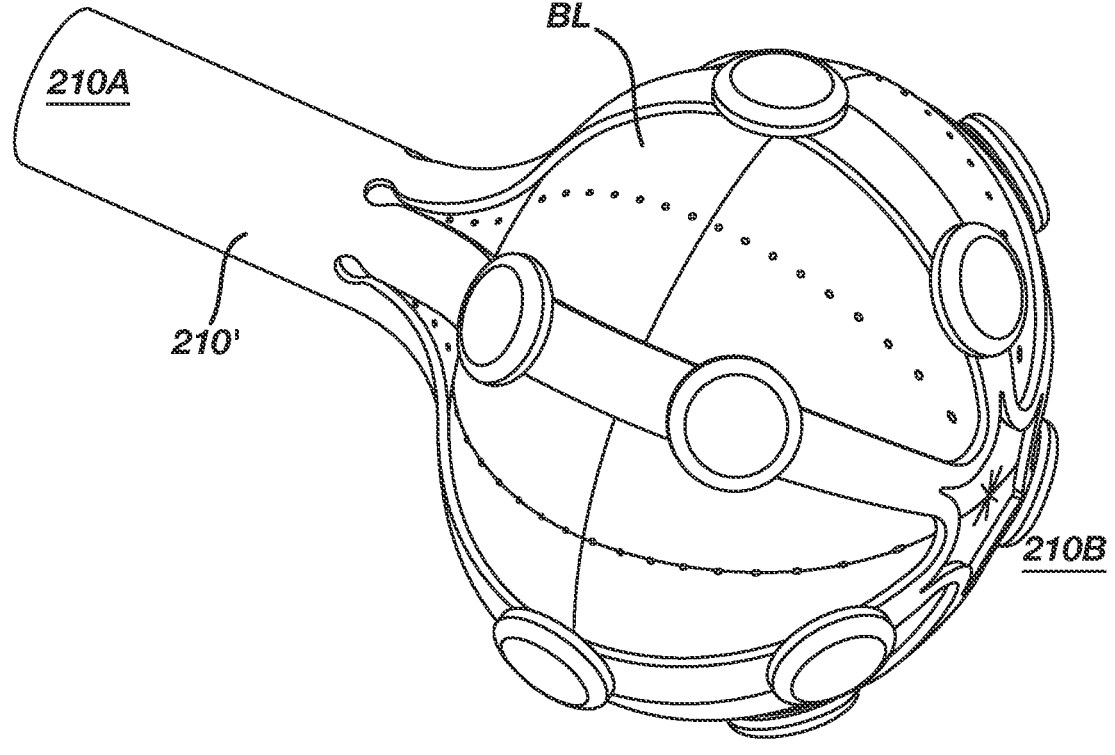
FIG. 10D illustrates an embodiment that relies on a balloon to expand the spine assembly, in accordance with an embodiment of the present invention.
Figure 10E:
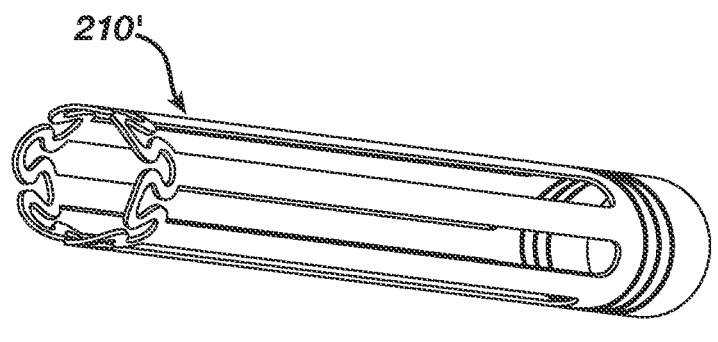
FIG. 10E illustrates a spine assembly formed by cutting a cylindrical tube stock with a laser, in accordance with an embodiment of the present invention.
Figure 10F:
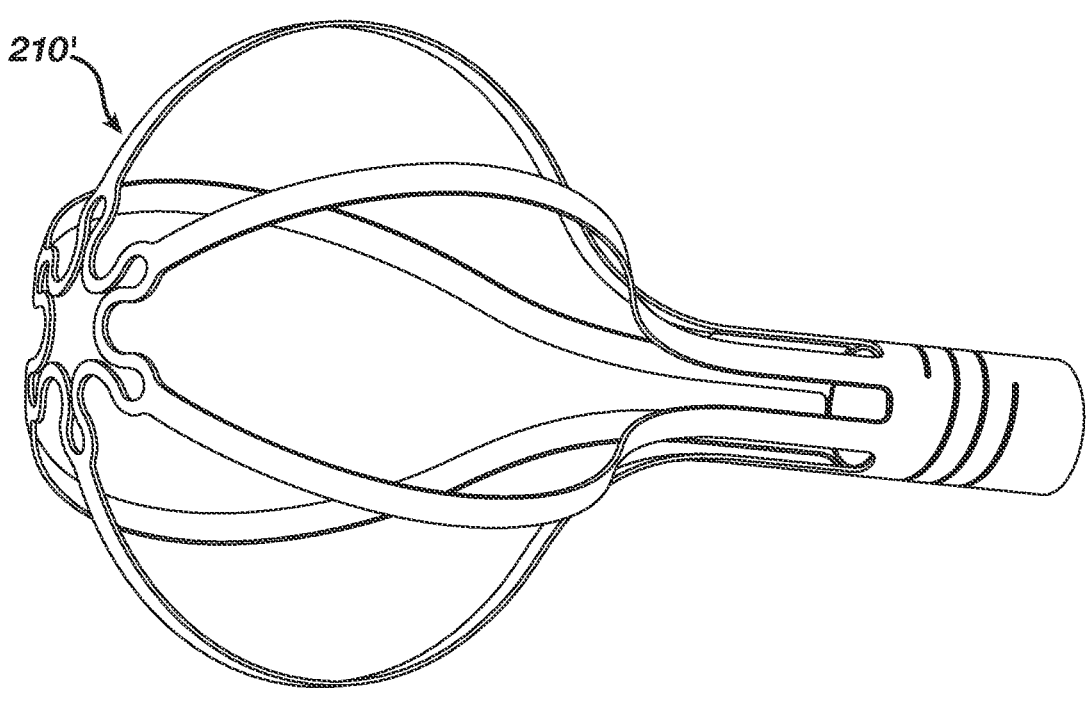
FIG. 10F illustrates a spine assembly after shape setting of the spines in FIG. 10E into a spheroidal basket like shape, in accordance with an embodiment of the present invention.

The spine assembly 210 can be physically connected to the tubular member 84 via a suitable technique such as adhesive or molding. In one embodiment shown here in FIG. 10C, eyelet 216a as well as locators 216b can be provided to aid in assembly as well as physical retention of the spines to the tubular member 84.

Where it is desired, a balloon BL can be provided as shown in FIG. 10D inside the spine assembly 210' to ensure full expansion of the spine assembly 210' from a cylindrical form factor into a spheroidal form as shown in FIG. 10C. In the embodiment of FIG. 10C, the spine assembly can be made from a tubular cylindrical stock material so that the proximal portion 210A and distal portion 210B are of one-piece material. The tubular stock is cut into a desired shape for the spine assembly 210' as shown in FIG. 10E. Thereafter, the cut tube can be shape set (or heat set) as is known by those skilled in the art to provide for the spheroidal spine configuration shown in FIG. 10F.

FIG. 11 is a flowchart illustrating a method 1100 of manufacturing a basket assembly 38, in accordance with an embodiment of the present invention. Method 1100 can include aligning 1102 a spine of an expandable basket assembly 38 with an electrode 40. The electrode can include two sections 441A, 441B that define a lengthwise direction of an electrode body section that tapers inward with respect to a central axis 87 of the respective electrode 40. Method 1100 can include inserting 1104 each spine into a lumen of at least one electrode 40. The electrodes 40 can be positioned such that the electrodes are offset between electrodes 40 on adjacent spines 214. Method 1100 can include fitting 1106 ends of the spine 216 to a tubular shaft 84 sized to traverse vasculature such that the central spine intersection 211 is positioned at a distal end 37 of the medical probe 22 and respective spines are movable from a tubular configuration to a bowed configuration. As will be appreciated by one of skill in the art including the benefit of this disclosure, fitting 1106 an end of the spine into a tubular shaft can include attaching the spine 214 to a spine retention hub 90. Furthermore, the spine retention hub 90 and/or the spine 214 and the tubular shaft 84 can be inserted into a flexible insertion tube 30 to form the medical probe 22

In some examples, the method can also include forming an approximately spheroid or oblate-spheroid shape with the linear spines. Method 1100 can further include electrically connecting the wire to the one or more electrodes. Method 1100 can also include disposing an insulative sleeve over the spine and within the lumen of the respective electrode.

Method can also include cutting a planar sheet of material 210 to form a plurality of linear spines 214 including a central spine intersection 211. Cutting the plurality of linear spines 214 can include cutting from a pattern including longitudinal and transverse scores. The planar sheet of resilient material can include shape-memory alloy such as nickel-titanium (also known as Nitinol), cobalt chromium, or any other suitable material. Method 1100 can include cutting a discrete cutout 214 at the central spine intersection 211. As described supra, the discrete cutout 214 can be a single cutout or two or more cutouts. In addition, the one or more discrete cutouts can be cut in a pattern to extend along at least a portion of each spine. In some examples, steps may occur as simultaneous steps or as a sequence of steps. As an alternative, metallic strands can shaped similar to the pattern formed by cutting the planar sheet.

As will be appreciated by one skilled in the art, method 1100 can include any of the various features of the disclosed technology described herein and can be varied depending on the particular configuration. Thus, method 1100 should not be construed as limited to the particular steps and order of steps explicitly described herein. It is noted that while the preference for the exemplary embodiments of the medical probe is for IRE or PFA, it is within the scope of the present invention to also use the medical probe separately only for RF ablation (unipolar mode with an external grounding electrode or bipolar mode) or in combination with IRE and RF ablations sequentially (certain electrodes in IRE mode and other electrodes in RF mode) or simultaneously (groups of electrodes in IRE mode and other electrodes in RF mode).

The disclosed technology described herein can be further understood according to the following clauses:

Clause 1: A medical probe, comprising: a tubular shaft including a proximal end and a distal end, the tubular shaft extending along a longitudinal axis of the medical probe; and an expandable basket assembly coupled to the distal end of the tubular shaft, the basket assembly comprising: a plurality of spines extending along the longitudinal axis and converging at a central spine intersection, the central spine intersection comprising one or more cutouts that allows for the spines to bow radially outward from the longitudinal axis when the expandable basket assembly is transitioned from a collapsed form to an expanded form, each spine of the plurality of spines comprising a plurality of electrodes, the respective electrode comprising an electrode body that defines a lumen therethrough such that the respective spine extends through the electrode body lumen, in which the respective electrode body comprises two sections that define a lengthwise direction of the electrode body that are inclined inward with respect to a central axis of the respective electrode.

Clause 2: The medical probe according to Clause 1, wherein the respective electrode body lumen comprises a first electrode width that tapers inwardly with respect to the central axis of the respective electrode body to form a second electrode width such that the first electrode width is larger than the second electrode width.

Clause 3: The medical probe according to any one of Clauses 1 or 2, wherein the respective electrode body comprises a curvature along the lengthwise direction of the electrode body.

Clause 4: The medical probe according to any one of Clauses 1-3, wherein a cross-sectional shape of each electrode comprises a substantially trapezoidal shape.

Clause 5: The medical probe according to any one of Clauses 1-4, wherein a cross-sectional thickness of each electrode comprises a dimension substantially similar to a cross-sectional thickness of the respective spine, and wherein the cross-sectional thickness of each electrode is configured to allow each electrode to bow radially outward from the central axis of the respective electrode body when the expandable basket assembly is transitioned from a collapsed form to an expanded form along the longitudinal axis.

Clause 6: The medical probe according to any of Clauses 1-5, wherein the plurality of spines extend from the central spine intersection in an equiangular pattern such that respective angles between respectively adjacent spines are approximately equal.

Clause 7: The medical probe according to any of Clause 1-6, further comprising a plurality of electrically insulative jackets each disposed between a respective spine of the plurality of spines and a respective electrode of the plurality of electrodes, thereby electrically isolating the plurality of electrodes from the plurality of spines.

Clause 8: The medical probe according to Clause 7, wherein each of the electrically insulative jackets of the plurality of electrically insulative jackets comprises a first lumen configured to receive the respective spine.

Clause 9: The medical probe according to Clause 7, wherein each of the electrically insulative jackets of the plurality of electrically insulative jackets comprises a first lumen and a second lumen, the first lumen configured to receive the respective spine and the second lumen configured to receive a first wire.

Clause 10: The medical probe according to any of Clauses 7-9, wherein a cross-sectional shape of each electrically insulative jacket comprises a substantially trapezoidal shape.

Clause 11: The medical probe according to Clause 1, wherein each respective spine of the plurality of spines comprises two electrodes.

Clause 12: The medical probe according to any of Clauses 1-11, further comprising a wire, wherein the electrode body lumen comprises a relief configured to receive the wire of the medical probe.

Clause 13: The medical probe according to Clause 12, wherein the wire is electrically connected to the electrode.

Clause 14: The medical probe according to any of Clauses 11-13, wherein at least a portion of the wire comprises an electrically conductive core material comprising a first electrical conductivity, an electrically conductive cover material comprising a second electrical conductivity less than the first electrical conductivity, the electrically conductive cover material circumscribing the electrically conductive core material, and an insulative jacket circumscribing the electrically conductive cover material.

Clause 15: The medical probe according to any of Clauses 11-13, wherein at least a portion of the wire comprises a plurality of strands and an insulative jacket circumscribing the plurality of strands, and wherein each strand of the plurality of strands respectively comprises an electrically conductive core material comprising a first electrical conductivity and an electrically conductive cover material comprising a second electrical conductivity less than the first electrical conductivity, the electrically conductive cover material circumscribing the electrically conductive core material.

Clause 16: The medical probe according to any one of Clauses 1-15, wherein the respective electrode of the plurality of electrodes comprises a wire relief adjacent the electrode body lumen to allow for the wire to extend adjacent to the electrode body lumen.

Clause 17: The medical probe according to Clause 16, wherein the electrode body lumen is disposed symmetrically about a longitudinal axis of the electrode body.

Clause 18: The medical probe according to any of Clauses 1-17, wherein the plurality of spines comprise a material selected from a group consisting of nitinol, cobalt chromium, stainless steel, titanium.

Clause 19: The medical probe according to any of Clauses 1-17, wherein the plurality of spines comprise a polymer.

Clause 20: The medical probe according to any of Clauses 1-19, wherein the plurality of electrodes is configured to deliver electrical pulses for irreversible electroporation, the pulses including a peak voltage of at least 900 volts (V).

Clause 21: The medical probe according to any of Clauses 1-20, wherein the plurality of spines is configured to form an approximately spherically-shaped basket assembly when in the expanded form.

Clause 22: The medical probe according to any of Clauses 1-20, wherein the plurality of spines is configured form an approximately oblate-spheroid basket assembly when in the expanded form.

Clause 23: The medical probe according to any of Clauses 1-22, further comprising spray ports configured to deliver an irrigation fluid to the plurality of electrodes.

Clause 24: A method of constructing a medical probe, the method comprising: aligning a spine of an expandable basket assembly with an electrode, the electrode comprising two sections that define a lengthwise direction of an electrode body section that taper inward with respect to a central axis of the respective electrode; inserting the spine into a lumen of the electrode; and fitting an end of the spine to a tubular shaft sized to traverse vasculature such that the expandable basket assembly is movable from a tubular configuration to a bowed configuration.

Clause 25: The method according to Clause 24, further comprising: positioning the spine of the expandable basket assembly through a first lumen of an electrically insulative jacket; positioning a wire through a second lumen of the electrically insulative jacket; positioning the electrode over the electrically insulative jacket; and electrically connecting the wire to the electrode through an aperture in the electrically insulative jacket providing passage between the second lumen and the electrode.

Clause 26: The method according to Clauses 24 and 25, wherein each respective spine of a plurality of spines comprises a first electrode and a second electrode, the method further comprising: aligning each respective spine of the plurality of spines with the first electrode and the second electrode; inserting each respective spine of the plurality of spines into a lumen of the first electrode and a lumen of the second electrode; and fitting an end of each respective spine of the plurality of spines to the tubular shaft sized to traverse vasculature.

Clause 27: The method according to any one of Clauses 24-26, further comprising offsetting the electrodes between adjacent spines.

Clause 28: The method according to any of Clauses 24-26, wherein the electrode body lumen is configured to receive a wire of the medical probe.

Clause 29: The method according to any of Clauses 25-28, wherein a cross-sectional shape of the electrically insulative jacket comprises a substantially trapezoidal shape.

Clause 30: The method according to any of Clauses 25-29, wherein the wire is insulated from the spine.

Clause 31: The method according to any of Clauses 25-30, wherein at least a portion of the wire comprises an electrically conductive core material comprising a first electrical conductivity, an electrically conductive cover material comprising a second electrical conductivity less than the first electrical conductivity, the electrically conductive cover material circumscribing the electrically conductive core material, and an insulative jacket circumscribing the electrically conductive cover material.

Clause 32: The method according to any of Clauses 25-31, wherein at least a portion of the wire comprises a plurality of strands and an insulative jacket circumscribing the plurality of the strands, and wherein each strand of the plurality of strands respectively comprises an electrically conductive core material comprising a first electrical conductivity and an electrically conductive cover material comprising a second electrical conductivity less than the first electrical conductivity, the electrically conductive cover material circumscribing the electrically conductive core material.

Clause 33: The method according to any of Clauses 24-32, wherein the plurality of spines comprise a material selected from a group consisting of nitinol, cobalt chromium, stainless steel, titanium.

Clause 34: The method according to any of Clauses 24-32, wherein the plurality of spines comprise a polymer.

Clause 35: The method according to any of Clauses 24-34, wherein a cross-sectional shape of the electrode comprises a substantial trapezoidal shape.

Clause 36: The method according to any of Clauses 24-35, further comprising configuring the electrode to deliver electrical pulses for irreversible electroporation, the pulses including a peak voltage of at least 900 volts (V).

Clause 37: The method according to any of Clauses 24-36, further comprising configuring the plurality of spines to form an approximately spherically-shaped basket assembly.

Clause 38: The method according to any of Clauses 24-36, further comprising configuring the plurality of spines to form an approximately oblate-spheroid-shaped basket assembly.

Clause 39: The method according to any of Clauses 24-38, further comprising configuring spray ports to deliver an irrigation fluid to the electrode.

Clause 40: A spine basket member comprising: a plurality of spines extending radially from a longitudinal axis; and a plurality of electrodes comprising an electrode body that defines a lumen therethrough such that each spine of the plurality of spines extends through the lumen, in which each electrode body comprises two opposing sections that define a lengthwise direction of the electrode body section that are inclined inwardly with respect to a central axis of the electrode body, and in which a cross-section of each electrode body comprises a substantially trapezoidal shape.

Clause 41: The spine basket member according to Clause 40, further comprising: a cutout defining a first open area of empty space proximate the longitudinal axis, the first open area of empty space approximating a first virtual circle including a first diameter from the longitudinal axis, the cutout extending into each of the plurality of spines for a first length to define an open slot in each of the plurality of spines, each slot being contiguous to a circumference of a second virtual circle greater than the first virtual circle.

Clause 42: The spine basket member of Clause 41, wherein one of every other slots on the plurality of spines includes an aperture defining a third area smaller than the first open area of empty space.

Clause 43: The spine basket member of Clause 42, in which the second virtual circle defines a second area of approximately 36 times that of the third area.

Clause 44: The spine basket member of Clause 43, in which the second area comprises approximately 7 times the first open area of empty space.

Clause 45: The spine basket member of Clause 42, in which the third area is about ¼ of the open first area while a total negative surface area of the cutout includes approximately 1.6 times the first open area of empty space.

Clause 46: The spine basket member of Clause 42, in which the third area comprises a circle with a radius includes approximately 0.4 times that of a first radius of the first virtual circle and a radius of the second virtual circle includes approximately 2.8 times that of the first radius.

Clause 47: The spine basket member of Clause 46, in which the first open area of empty space comprises approximately 2 mm-squared, the second area being approximately 15 mm-squared and the third area includes approximately 0.4 mm-squared and a total area of all cutouts includes approximately 3.5 mm-squared.

Clause 48: The spine basket member according to Clause 40, further comprising a tadpole shaped cutout on each of the plurality of spines, each cutout including a head portion contiguous to a circumference of a first virtual circle with a first radius disposed about the longitudinal axis, the head portion defining a negative area approximating a second virtual circle with a second radius, the head portion connected to a slotted tail portion extending for a first length along the spine and contiguous to an inside circumference of a third virtual circle including a third radius.

Clause 49: The spine basket member of Clause 48, in which the second radius includes approximately equal to that of a radius of the first virtual circle and the third radius includes approximately 8-15 times that of the radius of the first virtual circle.

Clause 50: The spine basket member according to Clause 49, in which the first length of the slotted tail portion includes approximately 6-10 times that of the length of the radius of the first virtual circle.

Clause 51: The spine basket member according to Clause 48, further comprising a cutout disposed on the longitudinal axis to define a central negative area approximating a central circle including a central radius smaller than the first radius.

Clause 52: The spine basket member according to Clause 48, in which the negative area of each of the tadpole cutouts includes approximately 0.2 mm-squared while the negative area of the central circle includes approximately 0.05 mm-squared so that the total negative area defined by all of the cutouts includes approximately 1.4 mm-squared.

Clause 53: The spine basket member according to Clause 48, in which central void radius comprises approximately 0.13 mm, the second radius comprises approximately 0.2 mm, and the first radius comprises approximately 0.23 mm.

Clause 54: The spine basket member according to Clause 48, in which the cutout defines a comet-shaped cutout with head portion with a slotted tapered tail extending to a proximal portion of each spine.

Clause 55: The spine basket member according to Clause 54, further comprising a circular hole located on the longitudinal axis of the spines with a central radius from the longitudinal axis.

Clause 56: The spine basket member according to Clause 55, wherein first radius includes approximately 90% of the central radius, the second virtual circle includes a second radius of approximately 2.5 times that of central radius while the third virtual circle includes a radius of approximately 10 times that of the central radius.

Clause 57: The spine basket member according to Clause 56, wherein each spine includes a first spine width that tapers towards the longitudinal axis to a smaller second spine width and further sub-dividing into two narrower spine arms running along the comet-shaped cutout by a portion comprising the comet-shaped cutout, each narrow spine arm including a third spine width.

Clause 58: The embodiments described above are cited by way of example, and the present invention is not limited by what has been particularly shown and described hereinabove. Rather, the scope of the invention includes both combinations and sub combinations of the various features described and illustrated hereinabove, as well as variations and modifications thereof which would occur to persons skilled in the art upon reading the foregoing description and which are not disclosed in the prior art.

What is claimed is:

1. A medical probe, comprising:
a tubular shaft including a proximal end and a distal end, the tubular shaft extending along a longitudinal axis of the medical probe; and
an expandable basket assembly coupled to the distal end of the tubular shaft, the basket assembly comprising:
    a plurality of spines extending along the longitudinal axis and converging at a central spine intersection, the central spine intersection comprising one or more cutouts that allows for the spines to bow radially outward from the longitudinal axis when the expandable basket assembly is transitioned from a collapsed form to an expanded form, each spine of the plurality of spines comprising a plurality of electrodes, the respective electrode comprising an electrode body that defines a lumen therethrough such that the respective spine extends through the electrode body lumen,
        in which the respective electrode body comprises two sections that define a lengthwise direction of the electrode body that are inclined inward with respect to a central axis of the respective electrode.

2. The medical probe according to claim 1, wherein the respective electrode body lumen comprises a first electrode width that tapers inwardly with respect to the central axis of the respective electrode body to form a second electrode width such that the first electrode width is larger than the second electrode width.

3. The medical probe according to claim 1, wherein the respective electrode body comprises a curvature along the lengthwise direction of the electrode body.

4. The medical probe according to claim 1, wherein a cross-sectional shape of each electrode comprises a substantially trapezoidal shape.

5. The medical probe according to claim 1, wherein each respective spine of the plurality of spines comprises two electrodes.

6. The medical probe according to claim 5, wherein the two electrodes are offset with respect to electrodes between adjacent spines.

7. A spine basket member comprising:
a plurality of spines extending radially from a longitudinal axis;
a plurality of electrodes comprising an electrode body that defines a lumen therethrough such that each spine of the plurality of spines extends through the lumen,
in which each electrode body comprises two opposing sections that define a lengthwise direction of the electrode body section that are inclined inwardly with respect to a central axis of the electrode body, and
in which a cross-section of each electrode body comprises a substantially trapezoidal shape; and
a plurality of electrically insulative jackets each disposed between a respective spine of the plurality of spines and a respective electrode of the plurality of electrodes, thereby electrically isolating the plurality of electrodes from the plurality of spines, wherein a cross-sectional shape of each electrically insulative jacket comprises a substantially trapezoidal shape.

8. A spine basket member comprising:
a plurality of spines extending radially from a longitudinal axis and a cutout defining a first open area of empty space proximate the longitudinal axis, the first open area of empty space approximating a first virtual circle including a first diameter from the longitudinal axis, the cutout extending into each of the plurality of spines for a first length to define an open slot in each of the plurality of spines, each slot being contiguous to a circumference of a second virtual circle greater than the first virtual circle;
a plurality of electrodes comprising an electrode body that defines a lumen therethrough such that each spine of the plurality of spines extends through the lumen,
in which each electrode body comprises two opposing sections that define a lengthwise direction of the electrode body section that are inclined inwardly with respect to a central axis of the electrode body, and
in which a cross-section of each electrode body comprises a substantially trapezoidal shape; and
a plurality of electrically insulative jackets each disposed between a respective spine of the plurality of spines and a respective electrode of the plurality of electrodes, thereby electrically isolating the plurality of electrodes from the plurality of spines.

9. The medical probe according to claim 1, further comprising a plurality of electrically insulative jackets each disposed between a respective spine of the plurality of spines and a respective electrode of the plurality of electrodes, thereby electrically isolating the plurality of electrodes from the plurality of spines.

10. The medical probe according to claim 9, wherein a cross-sectional shape of each electrically insulative jacket comprises a substantially trapezoidal shape.

11. The spine basket member of claim 8, wherein one of every other slot on the plurality of spines includes an aperture defining a third area smaller than the first open area of empty space.

12. A spine basket member comprising:
a plurality of spines extending radially from a longitudinal axis and a tadpole shaped cutout on each of the plurality of spines, each cutout including a head portion contiguous to a circumference of a first virtual circle with a first radius disposed about the longitudinal axis, the head portion defining a negative area approximating a second virtual circle with a second radius, the head portion connected to a slotted tail portion extending for a first length along the spine and contiguous to an inside circumference of a third virtual circle including a third radius;
a plurality of electrodes comprising an electrode body that defines a lumen therethrough such that each spine of the plurality of spines extends through the lumen,
in which each electrode body comprises two opposing sections that define a lengthwise direction of the electrode body section that are inclined inwardly with respect to a central axis of the electrode body, and
in which a cross-section of each electrode body comprises a substantially trapezoidal shape.

13. The spine basket member according to claim 12, further comprising a cutout disposed on the longitudinal axis to define a central negative area approximating a central circle including a central radius smaller than the first radius.

14. The spine basket member according to claim 12, in which the cutout defines a comet-shaped cutout with head portion with a slotted tapered tail extending to a proximal portion of each spine.

15. The spine basket member according to claim 12, further comprising a plurality of electrically insulative jackets each disposed between a respective spine of the plurality of spines and a respective electrode of the plurality of electrodes, thereby electrically isolating the plurality of electrodes from the plurality of spines.

16. The spine basket member according to claim 15, wherein a cross-sectional shape of each electrically insulative jacket comprises a substantially trapezoidal shape.

* * * * *